US011601742B2

(12) United States Patent
Anderson et al.

(10) Patent No.: US 11,601,742 B2
(45) Date of Patent: Mar. 7, 2023

(54) SYSTEMS, METHODS AND DEVICES FOR COMMUNICATION IN NOISY ENVIRONMENTS

(71) Applicant: INNOVERE MEDICAL INC., Markham (CA)

(72) Inventors: Kevan James Thompson Anderson, Cobourg (CA); Donald Bruce Plewes, Toronto (CA); Garry Ka Chun Liu, Etobicoke (CA); David Robert Green, Toronto (CA); Lynsie Alexandra Marie Thomason, Toronto (CA)

(73) Assignee: INNOVERE MEDICAL INC., Markham (CA)

( * ) Notice: Subject to any disclaimer, the term of this patent is extended or adjusted under 35 U.S.C. 154(b) by 874 days.

(21) Appl. No.: 16/464,386

(22) PCT Filed: Nov. 28, 2017

(86) PCT No.: PCT/CA2017/051427
§ 371 (c)(1),
(2) Date: May 28, 2019

(87) PCT Pub. No.: WO2018/094538
PCT Pub. Date: May 31, 2018

(65) Prior Publication Data
US 2020/0374615 A1    Nov. 26, 2020

Related U.S. Application Data

(60) Provisional application No. 62/427,072, filed on Nov. 28, 2016.

(51) Int. Cl.
*H04R 1/10*    (2006.01)
*H04R 1/02*    (2006.01)
(Continued)

(52) U.S. Cl.
CPC .......... *H04R 1/1016* (2013.01); *A61B 5/055* (2013.01); *A61F 11/10* (2013.01); *A61F 11/12* (2013.01);
(Continued)

(58) Field of Classification Search
CPC ....... A61B 5/055; A61B 5/7465; A61F 11/10; A61F 11/12; A61F 11/085; A61F 11/08;
(Continued)

(56) References Cited

U.S. PATENT DOCUMENTS

| 2,148,477 A | | 2/1939 | Koch | |
| 4,903,703 A | * | 2/1990 | Igarashi | ................. A61B 5/055 324/318 |

(Continued)

FOREIGN PATENT DOCUMENTS

| DE | 19727657 | 1/1999 |
| DE | 10343006 | 4/2005 |

(Continued)

OTHER PUBLICATIONS

Kenji Muto et al., "Voice communication system using bone-transmission device for MRI subjects" Journal of Tokyo Metropolitan College of 5 Industrial Technology, Japan, Mar. 20, 2007, p. 70-75, with an English Translation, 5 pages.

(Continued)

*Primary Examiner* — Brian Ensey
(74) *Attorney, Agent, or Firm* — Hill & Schumacher

(57) ABSTRACT

The present disclosure provides communication systems and devices for use in noise environments, such as during magnetic resonance imaging (MRI). In some embodiments, a communication headrest is provided that consists of a headrest that supports a patients' head, an optional bone conduction microphone, and one or more vibration actuators. The headset makes contact with noise-isolating ear- (Continued)

plugs worn by the subject such that vibrations generated by the vibration actuators are transferred through the earplug, via acoustic conduction, to enable the patient to hear audio content while the earplugs provide passive noise protection by occluding the ear canal. In other embodiments, active earplug devices are provided in which an acoustic transducer is contacted and supported by a noise isolating earplug, such that when the earplug is inserted into the ear canal, the acoustic transducer is brought into acoustic conductive communication with tissue surrounding the ear canal, facilitating acoustic communication through bone conduction.

22 Claims, 33 Drawing Sheets

(51) Int. Cl.
    *A61F 11/10*     (2006.01)
    *A61F 11/12*     (2006.01)
    *G01R 33/28*     (2006.01)
    *H04R 1/08*     (2006.01)
    *A61B 5/055*     (2006.01)
    *A61F 11/08*     (2006.01)

(52) U.S. Cl.
    CPC ........... *G01R 33/283* (2013.01); *H04R 1/028* (2013.01); *H04R 1/08* (2013.01); *A61F 11/085* (2022.01); *H04R 2460/13* (2013.01)

(58) Field of Classification Search
    CPC .... G01R 33/283; G16H 80/00; H04R 1/1016; H04R 1/028; H04R 1/08; H04R 2460/13; H04R 1/1083; H04R 1/1066; H04R 1/105
    See application file for complete search history.

(56) References Cited

U.S. PATENT DOCUMENTS

| | | |
|---|---|---|
| 5,295,193 A | 3/1994 | Ono et al. |
| 5,396,563 A | 3/1995 | Toshikazu |
| 5,577,504 A | 11/1996 | Salloway et al. |
| 5,602,478 A | 2/1997 | Salloway et al. |
| 5,692,059 A | 11/1997 | Kruger |
| 6,053,880 A | 4/2000 | Sleichter, III |
| 6,408,081 B1 | 6/2002 | Boesen |
| 6,661,901 B1 | 12/2003 | Svean et al. |
| 6,741,718 B1 | 5/2004 | Brumitt et al. |
| 6,920,229 B2 | 7/2005 | Boesen |
| 6,968,223 B2 | 11/2005 | Hanover |
| 7,088,840 B2 * | 8/2006 | Maekawa ............ H04R 1/1091 381/86 |
| 7,891,360 B2 | 2/2011 | Buck |
| 8,085,942 B2 | 12/2011 | Rasmussen |
| 8,103,014 B2 | 1/2012 | Porzelt et al. |
| 8,649,540 B2 | 2/2014 | Killion et al. |
| 8,675,897 B2 | 3/2014 | Fukuda et al. |
| 10,165,961 B2 * | 1/2019 | Alagappan ....... G01R 33/34046 |
| 2003/0112985 A1 | 6/2003 | Baumgart et al. |
| 2003/0161494 A1 | 8/2003 | Baumgart et al. |
| 2005/0018859 A1 | 1/2005 | Buchholz |
| 2005/0197565 A1 | 9/2005 | Yagi |
| 2007/0003096 A1 | 1/2007 | Nam |
| 2007/0012507 A1 | 1/2007 | Lyon |
| 2011/0193380 A1 | 8/2011 | Yamada |
| 2013/0188801 A1 | 7/2013 | Ambrose et al. |
| 2013/0317346 A1 | 11/2013 | Alagappan et al. |
| 2014/0093093 A1 | 4/2014 | Dusan et al. |
| 2014/0111206 A1 | 4/2014 | Kwon |
| 2014/0348346 A1 * | 11/2014 | Fukuda ................ H04R 1/1016 381/151 |
| 2014/0354283 A1 | 12/2014 | Kwon |
| 2015/0226816 A1 * | 8/2015 | Matschl ................ A61B 5/055 600/418 |

FOREIGN PATENT DOCUMENTS

| | | |
|---|---|---|
| DE | 102013218309 | 3/2015 |
| JP | 3175798 A | 7/1991 |
| JP | 200566021 | 3/2005 |
| JP | 2014200609 A | 10/2014 |
| JP | 201659435 A | 4/2016 |
| WO | 2012008419 A1 | 1/2012 |

OTHER PUBLICATIONS

International Search Report dated Feb. 19, 2018, in PCT/CA2017/051427 filed Nov. 28, 2017.

* cited by examiner

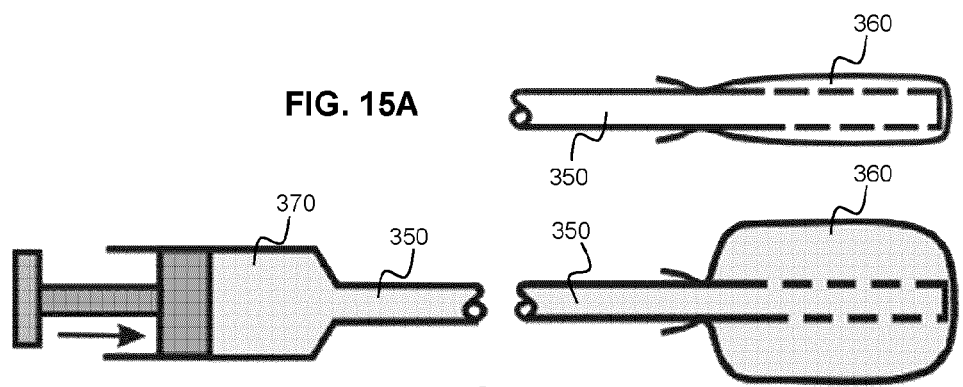
FIG. 15A
FIG. 15B
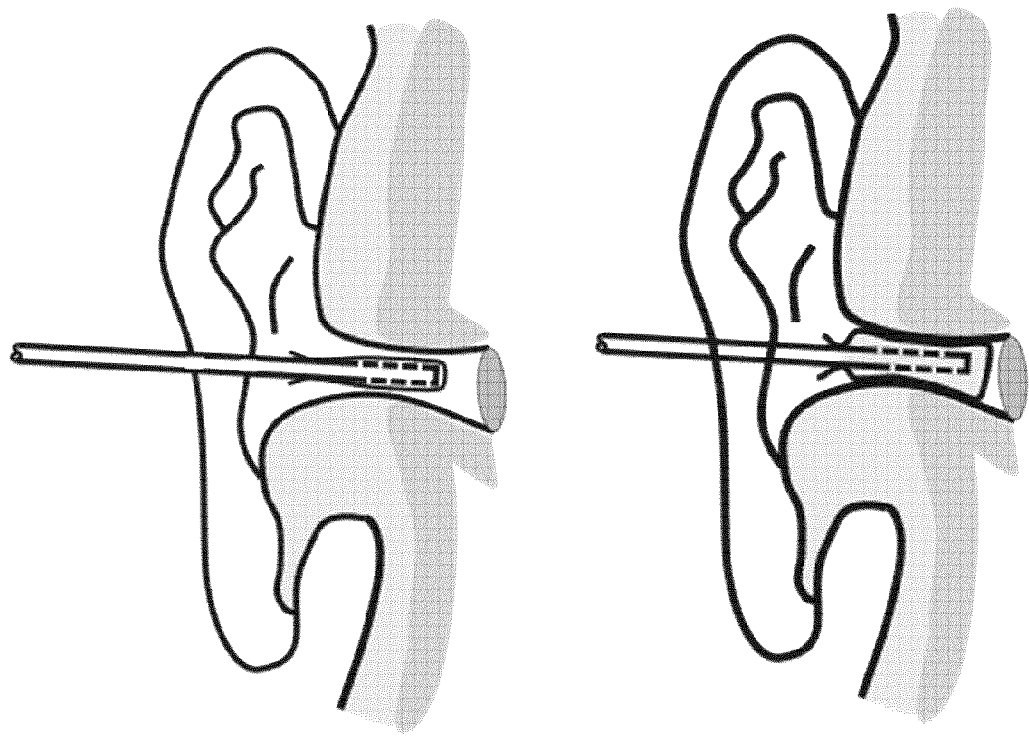
FIG. 15C
FIG. 15D

Frontal View

Side View

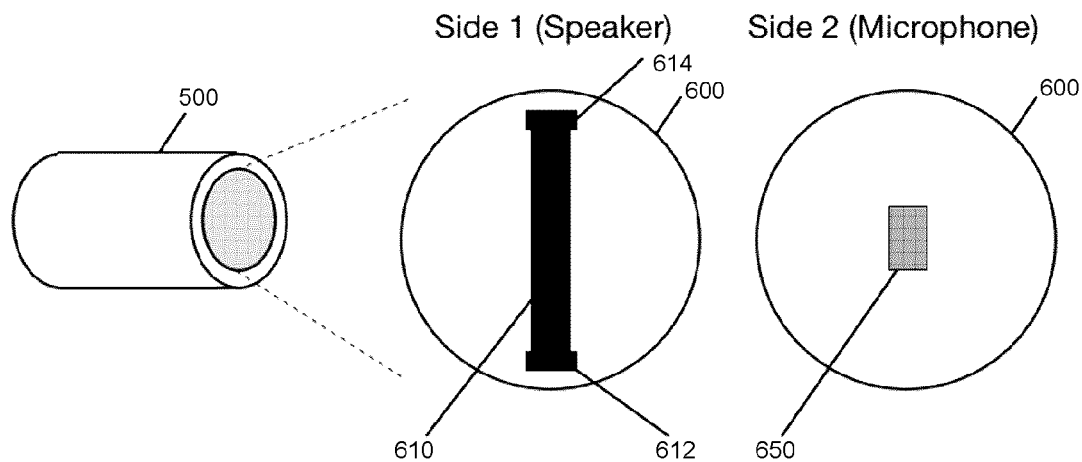
FIG. 28A  FIG. 28B  FIG. 28C
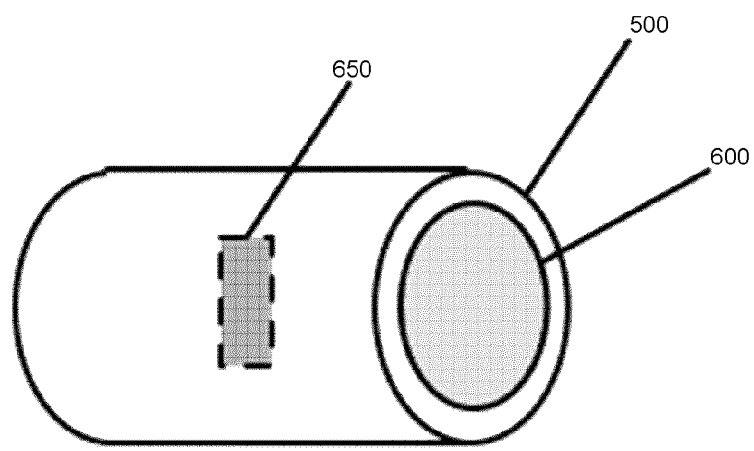
FIG. 29

SYSTEMS, METHODS AND DEVICES FOR COMMUNICATION IN NOISY ENVIRONMENTS

CROSS-REFERENCE TO RELATED APPLICATION

This application is a National Phase application claiming the benefit of the international PCT Patent Application No. PCT/CA2017/051427, filed on Nov. 28, 2017, in English, which claims priority to U.S. Provisional Application No. 62/427,072, titled "SYSTEMS, METHODS AND DEVICES FOR COMMUNICATION IN NOISY ENVIRONMENTS" and filed on Nov. 28, 2016, the entire contents of which are incorporated herein by reference.

BACKGROUND

The present disclosure relates to systems and methods for facilitating communication in noisy environments. More particularly, various aspects of the present disclosure pertain to patient communication systems and methods for use with magnetic resonance imaging.

Magnetic resonance imaging (MRI) systems are known to produce loud noise during scanning due to acoustic vibrations of gradient coils. Passive ear protection in the form of earplugs are typically provided to patients during an MRI scan. Such earplugs are very effective at reducing ambient noise and may achieve acoustic isolation greater than 30 dB. Due to the loud noise and the need for ear protection, communication with a patient presents challenges in the MRI environment. Communication with the scanning technologist is typically performed via a speaker and microphone located in the bore of the MRI scanner. However, due to the loud noise created by the scanner during operation, communication is typically limited to periods of non-operation in between the acquisition of images.

Several different patient communication systems have been developed to address this problem. For example, some patient communication systems employ air tubes with foam earplug ends, while other patient communication systems utilize wearable headsets with piezoelectric and other vibration actuators to facilitate communication with a patient.

Wearable headsets can be designed to provide a significant degree of passive noise isolation against ambient noise. However, in order to provide sufficient noise suppression for use with an MRI scanner, the headset needs to surround the ear with a large cavity or "muff". This can impose restraints for use in confined spaces such as a head coil. Air hoses are also frequently used to enable patient hearing, but generally provide poor passive noise isolation.

Other patient communication systems employ earplugs with air channels residing between the ear canal and an actuator supported by the earplug. Such systems may suffer from poor passive noise isolation due to the lack of occlusion of the ear canal.

Some patient communication systems employ optical microphones to facilitate communication from the patient to the scanning technologist. Such microphones need to be placed close the patient's mouth and their use in confined spaces (such as inside certain head coils) is therefore limited.

Other patient communication systems employ the use of bone conduction microphones, which can be utilized to detect speech with significant immunity to ambient noise and can therefore be used in noisy environments. Bone conduction microphones detect bone and tissue vibrations created by vocal cords. Commercial examples of vibration microphones utilize accelerometers, inertial sensors, and piezoelectric elements.

SUMMARY

The present disclosure provides communication systems and devices for use in noise environments, such as during magnetic resonance imaging (MRI). In some embodiments, a communication headrest is provided that consists of a headrest that supports a patients' head, an optional bone conduction microphone, and one or more vibration actuators. The headset makes contact with noise-isolating earplugs worn by the subject such that vibrations generated by the vibration actuators are transferred through the earplug, via acoustic conduction, to enable the patient to hear audio content while the earplugs provide passive noise protection by occluding the ear canal. In other embodiments, active earplug devices are provided in which an acoustic transducer is contacted and supported by a noise isolating earplug, such that when the earplug is inserted into the ear canal, the acoustic transducer is brought into acoustic conductive communication with tissue surrounding the ear canal, facilitating acoustic communication through bone conduction.

Accordingly, in a first aspect, there is provided an acoustic communication device for use during magnetic resonance imaging, the acoustic communication device comprising:

a headrest positionable within a magnetic resonance imaging scanner;

a vibration actuator supported by said headrest, wherein said vibration actuator is supported such that vibrations produced therefrom are acoustically coupled to an earplug worn by a subject when the subject's head is supported by said headrest, and such that the vibrations acoustically coupled to the earplug are acoustically coupled to tissues surrounding an ear canal of the subject, thereby enabling the subject to hear the vibrations via bone conduction; and audio circuity operably connected to said vibration actuator for sending audio signals thereto.

In another aspect, there is provided a bone conduction acoustic communication device comprising:

an elongate fluid conduit comprising a lumen;

an inflatable balloon in fluid communication with the lumen of said elongate fluid conduit;

means for introducing a fluid into said elongate fluid conduit, such that said balloon is inserted into an ear canal of a subject in a non-inflated state, subsequent introduction of the fluid into said elongate fluid conduit causes said balloon to inflate with the fluid and occlude the ear canal, thereby providing isolation from external acoustic noise; and an acoustic transducer contacting said elongate fluid conduit at a location remote from said balloon, such that when said balloon is inflated within the ear canal, said acoustic transducer is brought into acoustic conductive communication with tissue surrounding the ear canal via the fluid residing in said elongate fluid conduit and said balloon, thereby facilitating acoustic communication to and/or from the subject via bone conduction;

wherein said acoustic transducer is connectable to audio circuity for transmitting and/or receiving audio signals.

In another aspect, there is provided an acoustic communication device for communicating in a noisy environment, the acoustic communication device comprising:

a noise isolating earplug comprising a distal elongate portion that is insertable into an ear canal of a subject, such that upon insertion of said distal elongate portion into the ear canal, the ear canal is occluded over at least a portion of its extent, thereby providing isolation from external noise;

an acoustic transducer contacting and supported by said noise isolating earplug, wherein said acoustic transducer is supported such that when said distal elongate portion is inserted into the ear canal, said acoustic transducer is brought into acoustic conductive communication with tissue surrounding the ear canal via said distal elongate portion of said noise isolating earplug, thereby facilitating acoustic communication to and/or from the subject through bone conduction;

wherein said acoustic transducer is connectable to audio circuitry for transmitting and/or receiving audio signals.

In another aspect, there is provided an acoustic communication device for communicating in a noisy environment, the acoustic communication device comprising:

a headset configured to be worn on the head of a subject;

a vibration actuator supported by said headset, wherein said vibration actuator is supported such that vibrations produced therefrom are acoustically coupled to an earplug worn by the subject when said headset is worn by the subject, and such that the vibrations acoustically coupled to the earplug are acoustically coupled to tissues surrounding an ear canal of the subject, thereby enabling the subject to hear the vibrations via bone conduction; and audio circuitry operably connected to said vibration actuator for sending audio signals thereto.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 15A-D illustrate an example embodiments involving the use of a fluid-filled balloon as an earplug.

FIGS. 23-29 illustrate various active earplug devices in which multiple acoustic transducers are integrated with a noise isolating earplug for achieving two-way communication.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1A:
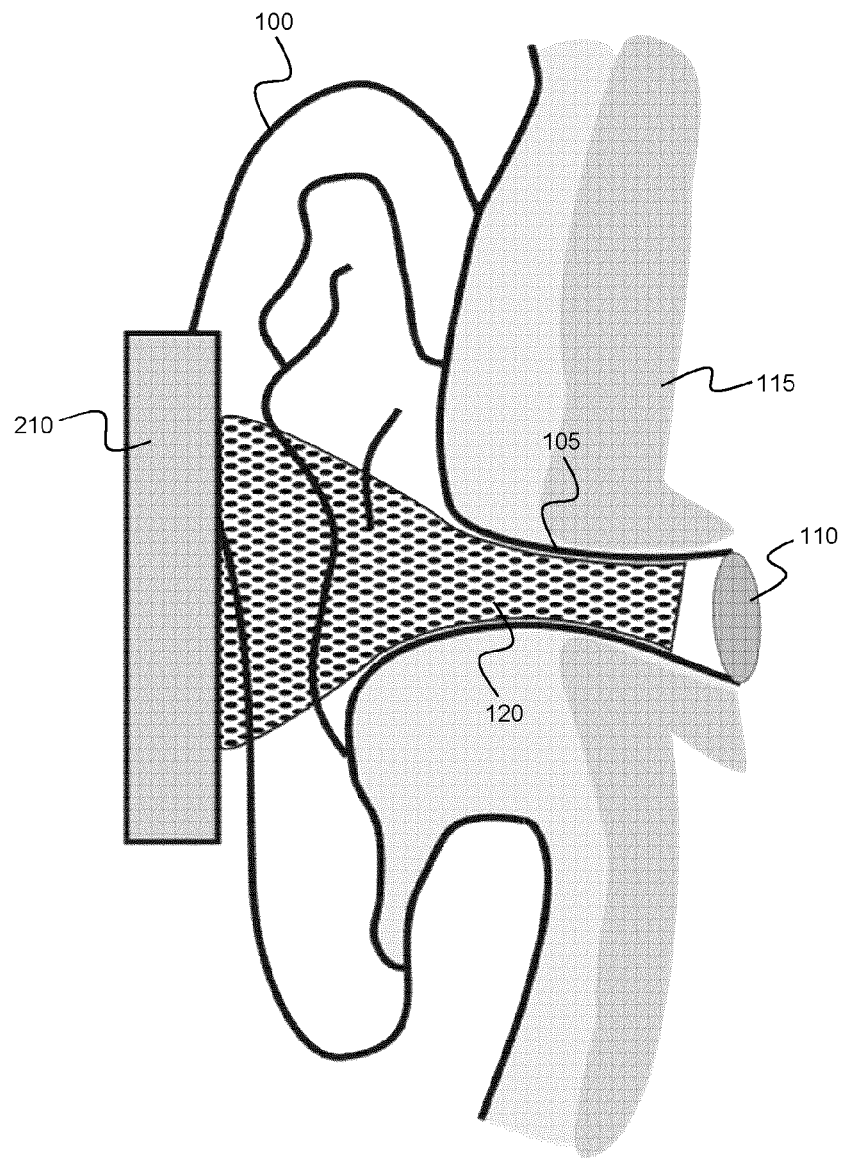
FIGS. 1A-E illustrate various example implementations of an acoustic communication system in which a vibration actuator is contacted with an earplug for acoustic coupling to a subject.

Various example embodiments of the present disclosure provide systems, devices and methods for facilitating communications in a noisy environment, such as within and nearby a magnetic resonance imaging (MRI) scanner. With reference to FIG. 1A, the aural anatomy is illustrated featuring the ear 100, the ear canal 105, the tympanic membrane 110 and the temporal bone 115. Also illustrated is an earplug 120 that occludes (obstructs) the ear canal, such that the earplug 120 provides the wearer with passive protection against loud ambient noise. A vibration actuator 210 is provided that contacts the earplug 120, and the vibration actuator is capable of producing vibrations at audio frequencies. Vibrations from the vibration actuator 210 are transferred to the earplug 120 as a result of the contact between the vibration actuator 210 and the earplug 120, the vibrations are conducted to the temporal bone 115 such that they are heard as sound by the wearer.

While the earplug 120 provides acoustic isolation against loud ambient noise, audio-frequency vibrations created by the vibration actuator 210 are conducted onto and through the earplug 120. These vibrations, which are conducted via the earplug 120 to the temporal bone 115 and surrounding soft-tissues, conduct sound to the inner ear and can be heard clearly by the patient through bone conduction.

Without intending to be limited by theory, it is believed that although bone conduction is a primary mechanism that enables the patient to hear sound generated by the vibration actuator 210, the transfer of vibrational energy from the proximal side of the earplug 120 into air, thereby generating sound waves within air in the ear canal (and the subsequent stimulation of the tympanic membrane) may provide a secondary mechanism for acoustic transduction. Both of these acoustic transduction mechanisms employ the conduction of vibrations from the vibration actuator 210 to the earplug via either direct physical contact between the vibration actuator 210 and earplug 120, or via indirect acoustic contact through an intermediate medium that also is able to conduct acoustic vibrations.

The vibration actuator 210 shown in FIG. 1 can be any device that creates vibrations from any type of electrical or mechanical input. Examples include, but are not limited to, piezoelectric crystals, piezoelectric actuators, piezoelectric benders, and magnetic speakers.

In one example embodiment, described in further detail below, the vibration actuator 210 may be a Lorentz speaker, for use in the static (main field; $B_0$) magnetic field of a MRI environment. A Lorentz speaker includes a membrane having an electrical trace defined thereon. When placed in a magnetic field, such as that of an MRI scanner, a Lorentz force is produced when current is passed through the trace. When the frequency of the current is at audio frequencies, acoustic vibrations of the membrane are created.

In one example implementation, the earplug 120 may be formed from, or include a viscoelastic polyurethane foam (e.g. "memory" foam; low-resilience foam), where the foam is compressed for insertion into the ear canal and expands to engage the ear canal to provide effective passive noise cancellation. Passive noise protection of up to 35 dB is common for earplugs formed from viscoelastic polyurethane foam. Viscoelastic polyurethane foams (memory foams) have the defining material property that they soften when heated to 37 degrees Celsius (human body temperature) and can therefore be molded to a warm body such as the cavity of the ear canal. In addition, memory foams have the property that they return to their original molded shape. Viscoelastic polyurethane foam is a suitable material for earplugs, and is often provided as a cylindrical volume of viscoelastic polyurethane foam that can be compressed and inserted into the ear canal. Upon insertion, the foam expands and molds to the ear canal to form an occlusion with firm and even contact on the inner surface of the ear canal.

In alternative example implementations, other materials may be employed to fit within the ear canal to provide passive noise isolation. Non-limiting examples of such materials include waxes, silicone, non-memory foams, and soft plastics.

In some example implementations, an earplug may be formed having structural features that permit convenient insertion while occluding the ear canal. For example, with reference to FIG. 1B, an earplug is illustrated where the portion of the earplug that is insertable into the ear canal includes one or more flexible ridges that are provided to mechanically support the earplug in the ear canal while occluding the ear canal. Such ridges could be constructed out of flexible materials, including but not limited to, silicone or flexible thermoplastics.

As described above, the earplug 120 is capable of conducting or transmitting vibrations at audio frequencies, such that vibrations generated by the vibration actuator 210 are conducted to the temporal bone, thereby facilitating an acoustic path within the ear canal that enables bone conduction.

As described above, the earplug 120 facilitates the conduction of vibrations to the temporal bone. To ensure efficient transfer of pressure waves traveling in the direction parallel to the earplug-temporal bone interface, the earplug is configured to provide mechanical contact with the tissues adjacent to the temporal bone. This can be achieved by proving an earplug having a size, shape and/or elasticity that causes the outer surface of the insertable portion of the earplug to physically contact the inner surface of the ear canal over at least a portion of the length of the ear canal.

In order to facilitate efficient transfer of pressure waves traveling in the direction perpendicular to the earplug-temporal bone interface, the earplug may be constructed from a material having a density that is similar (such as within the same order of magnitude; i.e. within 10×) to that of the tissues that surround the ear canal and temporal bone. For example, the inventors have found that an earplug made out of viscoelastic foam with a mass density of 0.25 g/cc effectively couples sound that can be heard by the wearer. It is expected that suitable coupling will be achievable for materials with a mass density ranging from approximately 0.2 g/cc-20 g/cc. As another illustrative example, a very porous material with a density similar to that of air (density of 0.001 g/cc) does not effectively couple sound that can be heard by the wearer. Examples of such materials include, but are not limited to viscoelastic memory foams as described above, or plastics, waxes, thermoplastics, polymers, or composites of such materials.

Figure 1B:
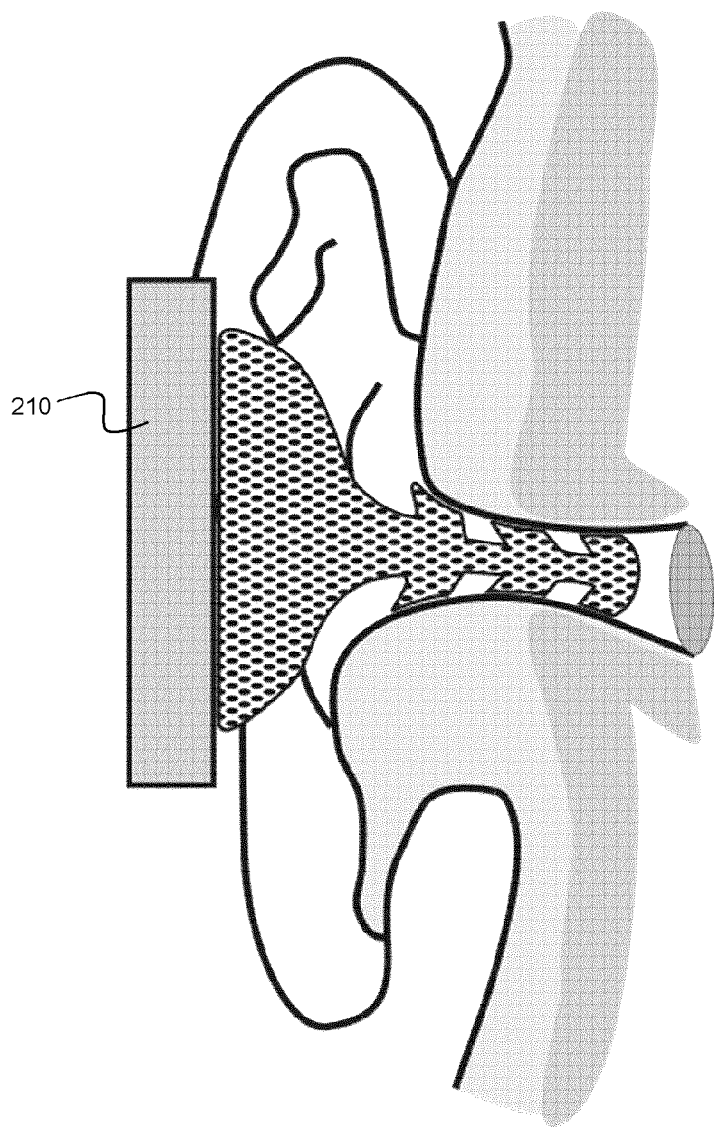

It will be understood that the vibration actuator 210 shown in FIGS. 1A and 1B may be contacted with the earplug 120 according to a wide variety of embodiments and implementations. Furthermore, as described in detail below, it will be understood that the vibration actuator 210 need not make direct mechanical contact with the earplug 210, and that one or more additional solid or liquids may be provided between the vibration actuator 210 and the earplug 120 in order to facilitate the coupling (transfer) of vibrations generated by the vibration actuator 210 to the earplug 120 (in the absence of sound propagation in air). In other words, the vibration actuator 210 may be brought into acoustic conductive communication with the earplug 120 via direct contact, or indirect contact via one or more acoustic coupling materials or structures. As described further below, one or more acoustic coupling material may be selected to have respective acoustic impedances that support the efficient acoustic conduction of vibrations from the vibration actuator 210 to the earplug 120.

In some example embodiments, the vibration actuator 210 is supported by an external support, such that when the patient's head is brought into contact with the external support, acoustic vibrations generated by the vibration actuator 210 are conducted to the earplug 120 (in the absence of sound propagation in air). For example, as described in several of the forthcoming example embodiments, the vibration actuator 210 may be attached to, embedded within, or otherwise supported by a headrest, such that when the patient's head is supported by the headrest, acoustic vibrations generated by the vibration actuator 210 are coupled to the earplug.

In other example embodiments, active earplugs are described, in which the vibration actuator is attached to, embedded within, integrated within, or otherwise supported by the earplug.

Figure 1C:
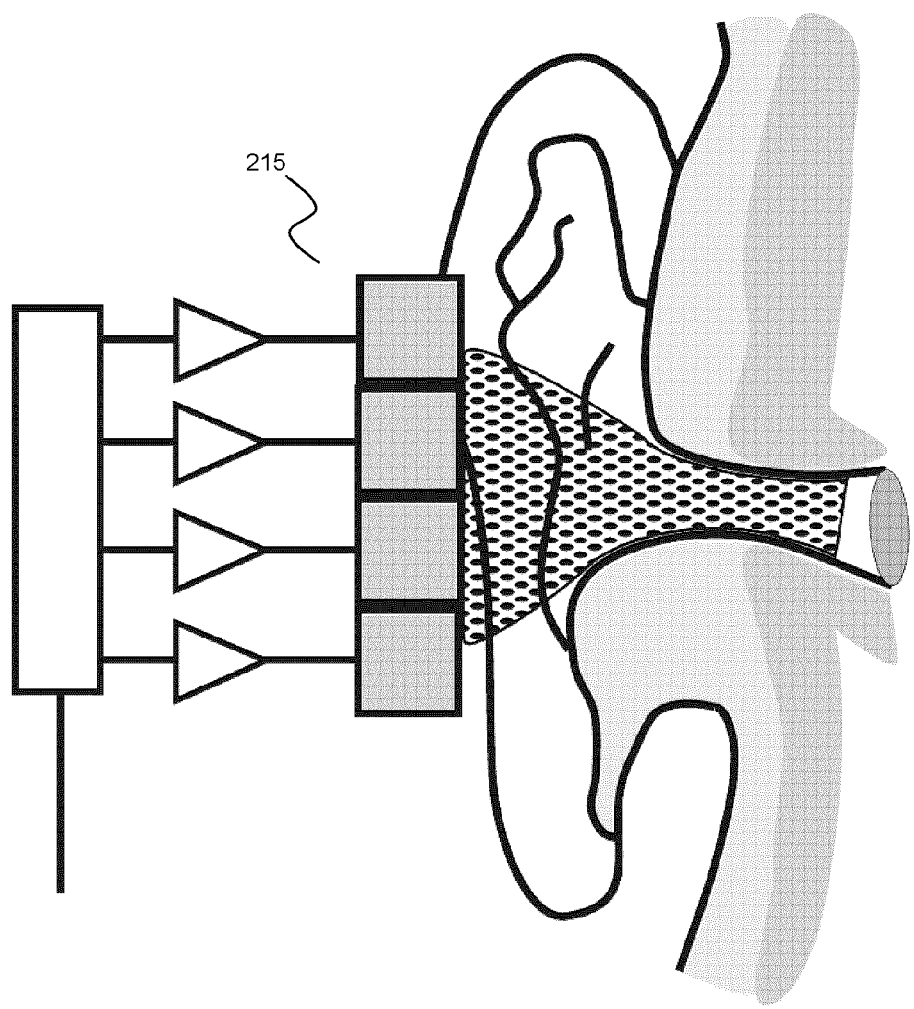
Figure 1D:
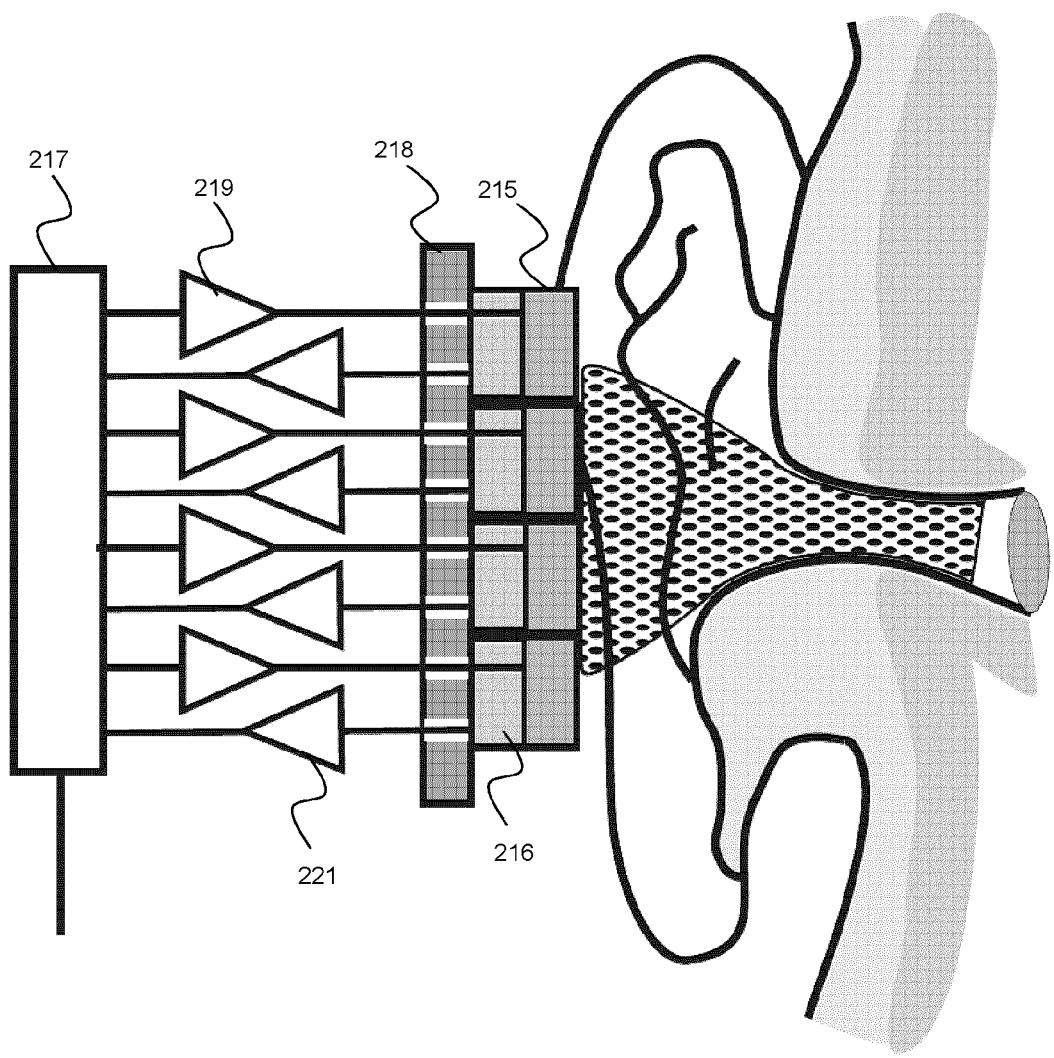

In some example embodiments, a plurality of vibration sources may be provided, as shown in FIGS. 1C and 1D. This would ensure that proper contact between the vibration source and the ear plug is achieved without tedious manipulation of the patient's position. Once configuration would involve an array of rigid vibration sources 215, some of which would be in more uniform or complete contact with the ear plug. This could be determined by placing in contact with the vibration sources an array of pressure transducers 216 which could be formed from piezoelectric strain gauges or load cells. The array of pressure transducers and vibratory sources could be mounted on a rigid plate 218 through which electrical connections are made to their respective amplifiers. Each vibratory source would be powered by audio amplifiers 219 while the signal from each pressure transducer would be detected and amplified by an array of pre-amplifiers 221.

After placement of the array on the patient's out ear, the signals from the pressure transducers would be sampled and from this transducer with the greatest contact pressure would be chosen for delivery of the vibratory source. Alternatively, more than one vibratory source could be actuated depending on the distribution of pressure detected from the pressure transducers. These signals would be analyzed by audio electronics 217 and the audio signals delivered to the patient.

Figure 1E:
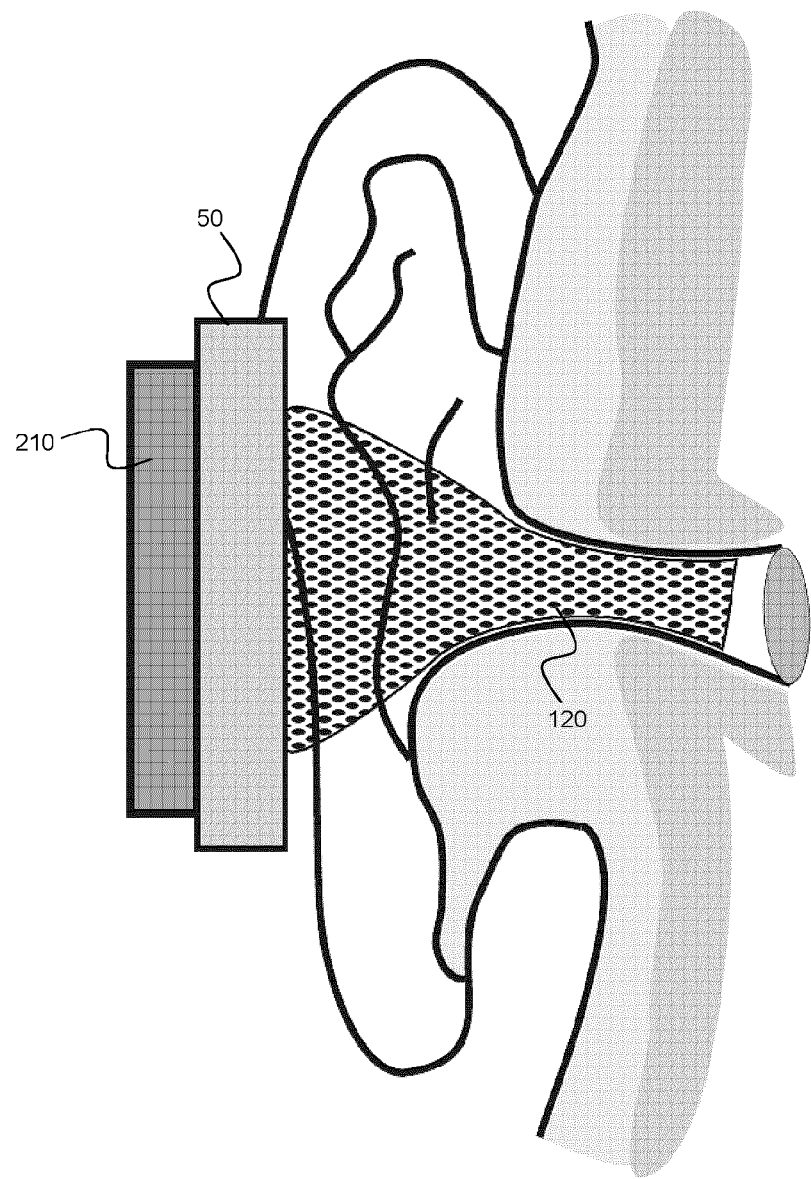

As shown in FIG. 1E, in order to ensure appropriate delivery of vibratory motion to the ear plug, a material of suitable density and stiffness could be interposed between the ear plug and the vibratory source. An impedance matching layer 50 would be bonded to the patient side of the vibratory source 210 and placed in contact with the ear plug 120.

Figure 2A:
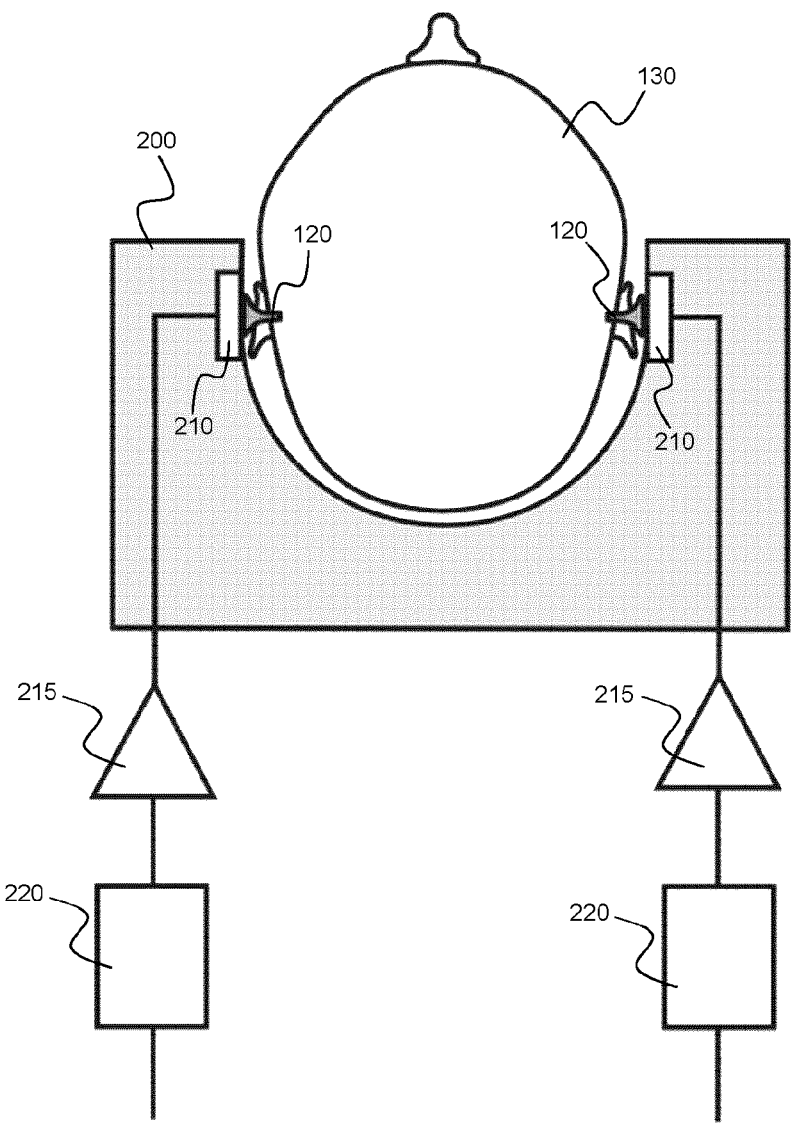
FIGS. 2A-B show overhead views of two example acoustic communication systems.

FIG. 2A illustrates an example embodiment of a headrest-based communication system for use during MRI scanning. A head support headrest 200, for use within the bore of an MRI scanner, supports the head of the patient 130. Vibration actuators 210 are incorporated (e.g. recessed) into the headrest 200 such that they make physical contact with the outside surface of earplugs 120 wore by the patient while the patient's head 130 is supported by the headrest 200. The communication headrest 200 may be employed to facilitate communication from a scanning technologist to the patient, and may additionally or alternatively be employed to allow the patient entertainment content, such as music, audiobooks, or movies during the scanning operation of the MRI scanner.

Although the vibration actuators 210 are illustrated as being recessed (inset) into the headrest 200, the vibration actuators 210 could alternatively be affixed to the surface of the headrest 200 that is adjacent to the position of the patient's ears.

As shown in FIG. 2A, each vibration actuator is electrically connected to an amplifier 215 and electronics 220 that are designed to vibrate the vibration actuator 210. For example, in the case where the vibration actuator 210 is a piezoelectric device, a class G ceramic speaker driver such as the MAX9788 could be used drive the device based on an audio signal supplied by a Bluetooth receiver module. In the case where the vibration actuator was a Lorentz speaker, a class A or A/B amplifier such as the MAX98309 could be used drive the device based on an audio signal supplied by a received from a Bluetooth receiver module. It should be understood that one that is skilled in the art will be able to select the appropriate electronics for use with a specific type of vibration actuator 210.

In some example implementations, each vibration actuator 210 may be spatially offset from the position where the headrest 200 makes contact with the earplug 120, provided that vibrational energy is conducted through the an intermediate material to the earplug without substantial attenuation. For example, in one non-limiting example embodiment, a vibration actuator 210 could be placed between 1 cm and 20 cm and, depending on the material properties of the headrest 200, this spatial offset could result in attenuation of the vibrations between −0.01 and −20 db, thereby still enabling a non-negligible about vibrational energy to be transferred to the earplug 120. Moreover, the attenuation may be compensated by increasing the power of the vibration actuators 210.

Figure 2B:
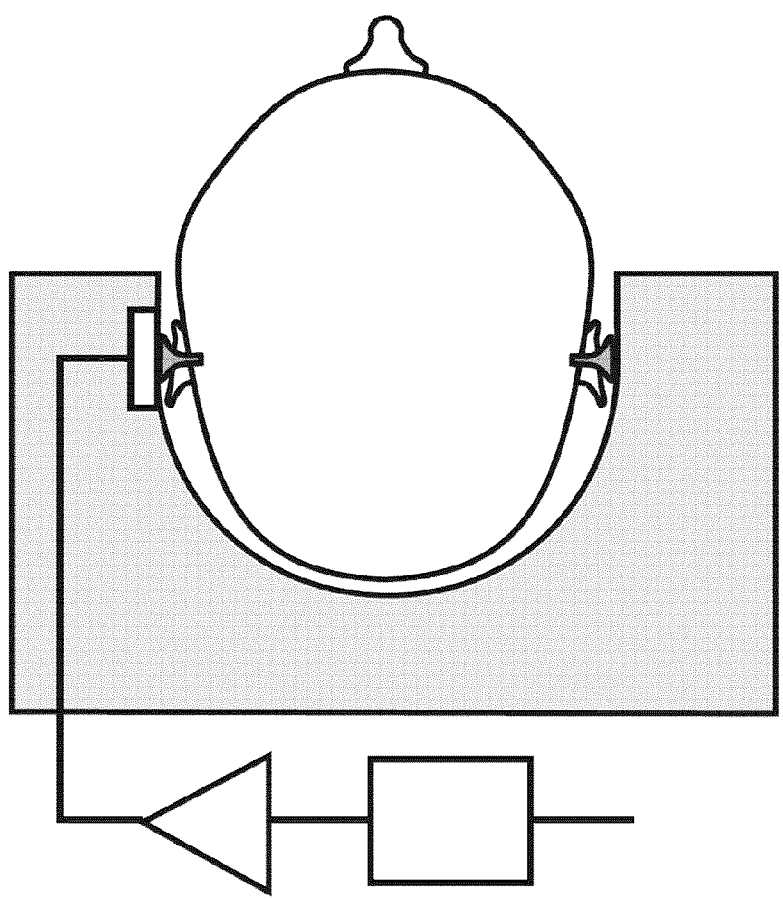

Although many of the present example embodiments show dual-actuator embodiments involving vibration actuators on either side of the head, it will be understood that any of the embodiments may be adapted to provide single-sided versions having one or more vibration actuators on one side of the head. FIG. 2B shows an example of such an embodiment.

Figure 3:
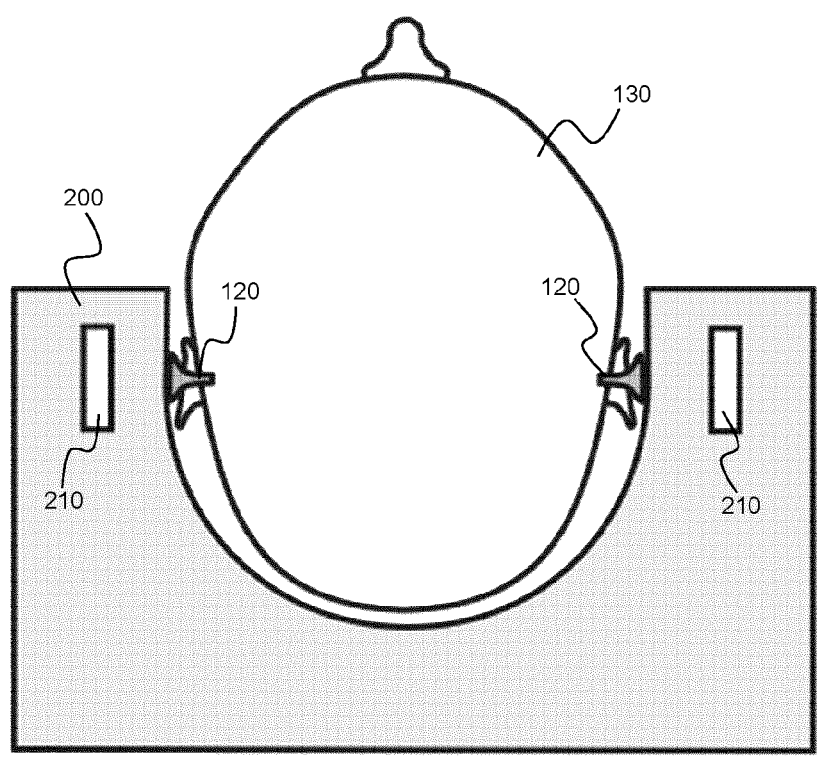
FIG. 3 illustrates an example communication system in which vibration actuators are embedded within a headrest.

FIG. 3 illustrates one such example embodiment where the vibration actuators 210 are embedded within the headrest 200 and are spatially offset from the location where the headrest makes contact with the earplug 120, such that the headrest material between the vibration actuators 210 and the earplugs 120 provides a coupling medium that indirectly places the vibration actuators 210 in acoustic conductive communication with the earplugs 110. Unlike the example embodiment shown in FIG. 2A in which the vibrations generated by each vibration actuator are directly coupled to each earplug, the vibrations produced from the vibration actuators 210 shown in FIG. 3 are conducted through a length of headrest material prior to being transferred onto the outer surface of the earplug 120.

In one example implementation, the acoustic impedance of the headrest material and the earplug material may be selected to enable effective vibrational energy transfer between the headrest 200 and the earplug 120. Impedance mismatches can lead to acoustic reflections and inefficiencies. For example, the materials may be selected so that the transmission coefficient of acoustic power through the material interface is greater than 20%, where the transmission coefficient for acoustic power can be calculated as $1-[(Z_{headrest}+Z_{earplug})/(Z_{headrest}-Z_{earplug})]^2$, where $Z_{headrest}$ is the acoustic impedance of the headrest and $Z_{earplug}$ is the acoustic impedance of the earplug material. This condition is met if the acoustic impedance of the headrest material and the earplug material are within 10 times of each other.

It will be understood that the although vibration actuators 210 are illustrated in many of the example embodiments as being aligned such that vibrations produced therefrom are emitted parallel to a longitudinal axis of the earplug 120, the a vibration actuator 210 can be offset or rotated with respect to each earplug longitudinal axis, provided that such offset or rotation does not result in substantial acoustic coupling loss.

Figure 4A:
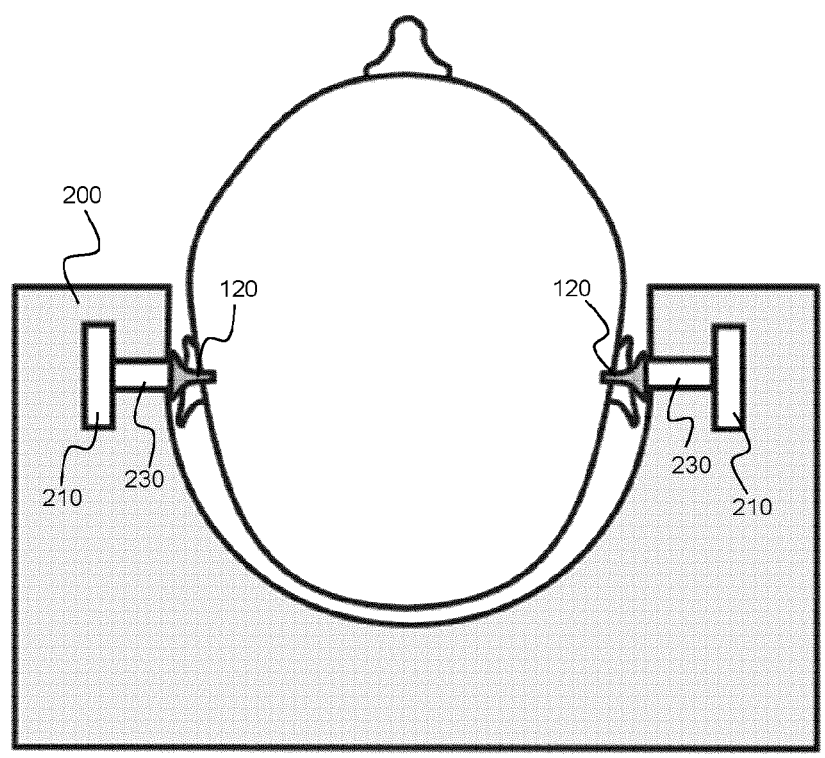
FIGS. 4A-B illustrate example communication systems in which an acoustic channel is provided between each vibration source and earplug.

FIG. 4A illustrates an alternative example embodiment in which an acoustic conduit 230 (e.g. a pillar or other component) of acoustically conducting material is embedded within the headrest 200 in order to facilitate the acoustic conduction of vibrational energy from the vibration actuators 210 to the earplugs 120. The acoustic conduit 230 is formed from an acoustically conductive material selected to facilitate conduction of acoustic energy from the vibration actuator 210 to the earplug 120. Examples of suitable materials for forming the acoustic conduit 230 include, but are not limited to, materials that are capable of conducting vibrational energy to the earplug without attenuating the energy by more than 20 db and have are acoustic matched such that the transmission coefficient of vibrational energy is at least 20%. Non-limiting examples of such materials include waxes, silicone, non-memory foams, and soft plastics.

The acoustic conduits 230 may be arranged such that distal ends thereof reside at, or adjacent to, the outer surface of the headrest. In one example implementation, the distal ends of the acoustic conduits 230 may be located at the headrest surface. In another example implementation, the distal ends of the acoustic conduits 230 may protrude outwards (extend outwards) from the headrest surface.

Figure 4B:
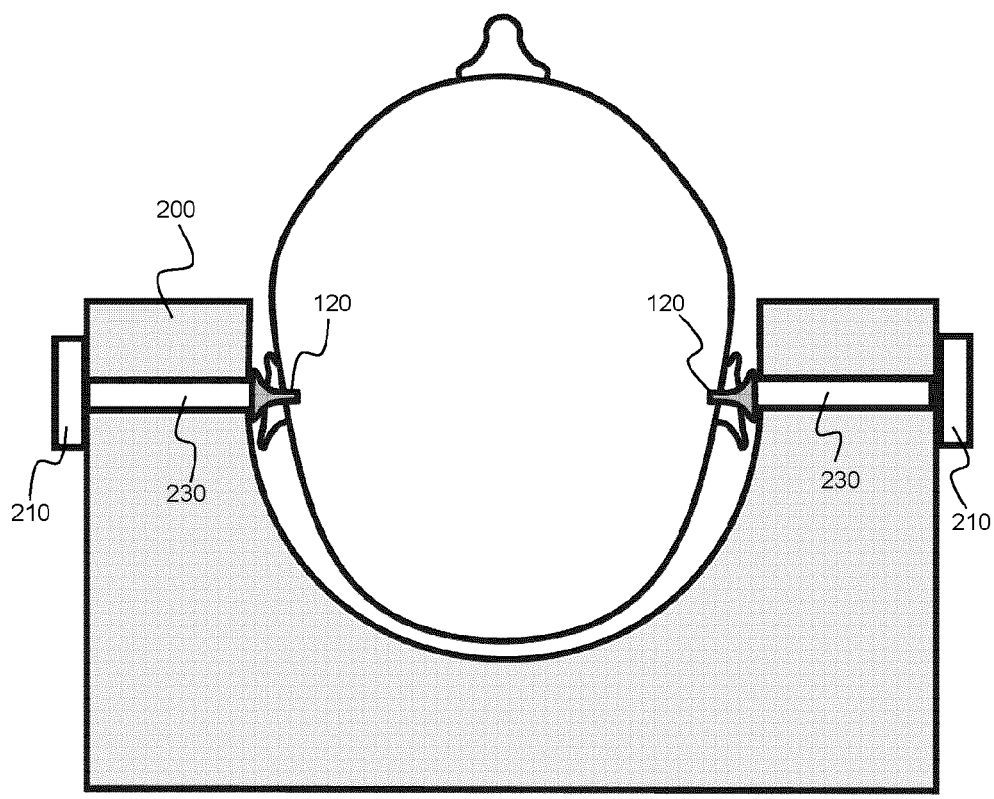

FIG. 4B illustrates an alternative example embodiment in which an acoustic conduit 230 extends through the headrest 200 to provide an acoustically conductive path (channel, conduit) between vibration actuators 210 that on or beyond an external surface of the headrest 200 (or recessed into an external surface of the headrest 200).

In some embodiments, a headrest communication system may be adapted to support bi-directional (two-way) communication by integrating a bone conduction microphone into the headrest, such that the headrest is capable of transmitting acoustic vibrations to the patient via the contact between the vibration actuators 210 and the earplugs 120, and also detecting, via the bone conduction microphone, speech generated by the patient.

Figure 5:
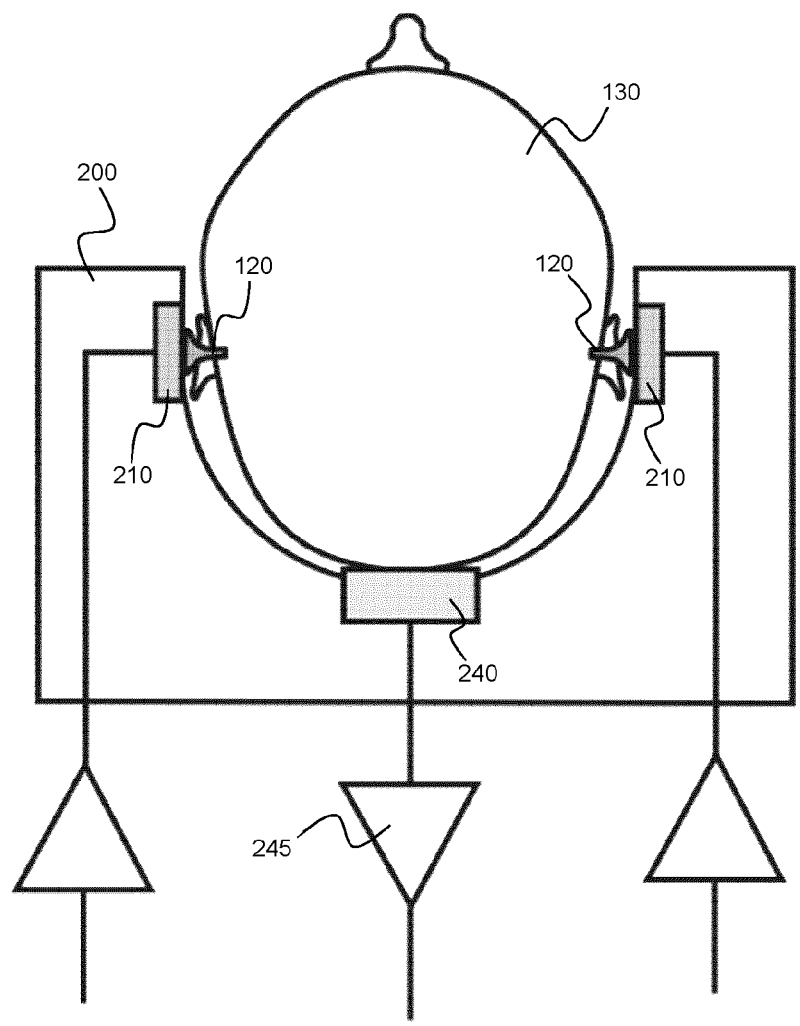
FIG. 5 illustrates an example communication system in which the headrest includes a bone conduction microphone.

FIG. 5 illustrates an example of such a headrest-based communication system, in which a headrest 200 is shown supporting a patient's head 130, where the headrest 200 includes embedded vibration actuators 210 that make contact with earplugs 120 worn by the patient and a bone conduction microphone that is embedded in the headrest 200. The bone conduction microphone 240 makes contact with the back of the patient's head to enable the reception of the patient's voice. During speech, vibrations originating at the vocal cords are transferred to bony structures such as the skull. These vibrations can be detected by the bone conduction microphone 240 and converted into an electrical signal to be represented as speech. Because speech sensing is performed based on acoustic vibrations, as opposed to the propagation of sound waves in air, the bone conduction microphone 240 has poor sensitivity to ambient noise in the form of propagating sound waves. The bone conduction microphone 240 is therefore not sensitive to the loud noises of the MRI scanner, thereby enabling effective communication between the patient other individuals, such as the scanning technologist, during the operation of the MRI scanner. It will be understood that a bone conduction microphone may be integrated with any of the preceding example headrest communication systems, and variations thereof.

This example embodiment illustrates an acoustic communication system in which two-way acoustic communication is facilitated in the absence of sound wave propagation, whereby the vibration actuators 210 and the bone conduction microphone 240 enable acoustic communication based on the acoustic conduction of vibrations to and from the patient.

It will be understood that the bone conduction microphone 240 may be implemented according to a wide range of acoustic transducers that are suitable for detecting acoustic vibrations. For example, in some non-limiting example implementations, the vibration microphone 240 may include an accelerometer, velocity sensor, proximity probe, piezoelectric crystal, or piezoelectric bender.

Alternatively, in another example implementation, the bone conduction microphone may be implemented using a Lorentz microphone, where a Lorentz acoustic speaker is employed in a reciprocal mode where an electric potential is induced across conductors vibrating in the magnetic field of the MRI. In this example, the bone conduction microphone 240 can be operably connected to additional electronics 245, including, but not limited to, an amplifier, processor, and/or wireless transmitter. It will be understood that the skilled artisan will be capable of selecting the appropriate electronics associated with the specific type of the bone conduction microphone used in a given implementation.

Figure 6:
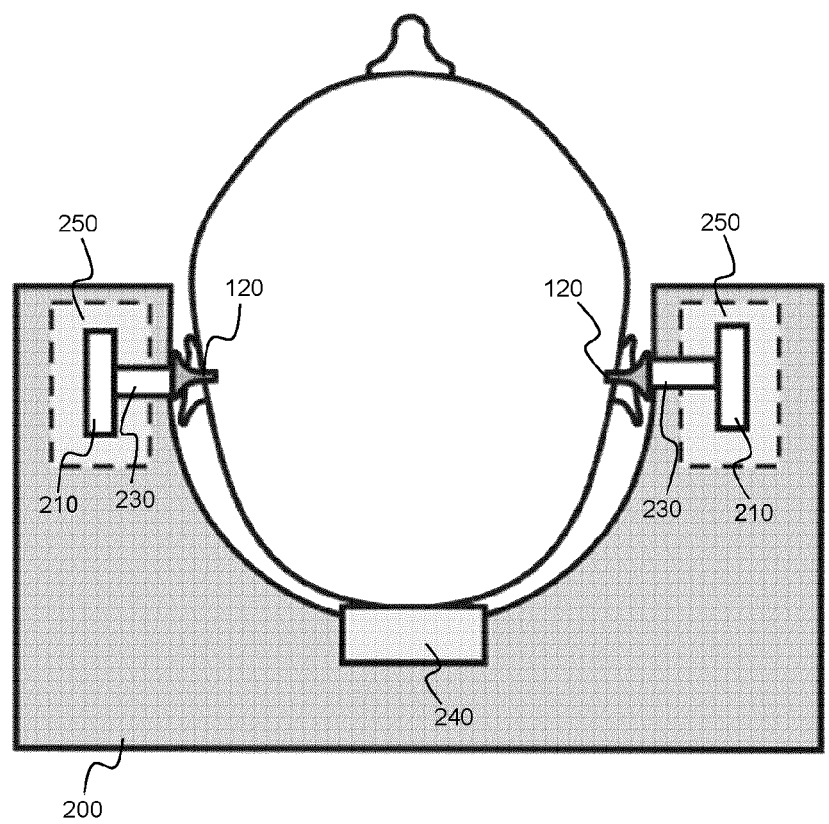
FIG. 6 illustrates an example communication system in which the vibration actuators are provided in acoustic isolation regions.

With reference to FIG. 6, an example embodiment is illustrated in which the vibration actuators 210 are supported within respective acoustically isolating regions (e.g. chambers) 250 that are also embedded inside (or alternatively recessed within) the headrest 200. The acoustically isolating regions 250 reduce the intensity of vibrations that are coupled from the vibration actuators 210 into the headrest 200 along directions other than the direction between the vibration actuators 210 and the earplugs 120, thereby reducing the intensity of spurious vibrations detected by the bone conduction microphone 240.

Acoustic conduits 230, formed from an acoustically conductive material (as described above), may also be embedded in the headrest 200 to provide an acoustically conductive path for conducting vibrations from the vibration actuator 210 to the earplug 120. In the example embodiment shown in FIG. 6, each acoustic conduit 230 extends through an aperture in the wall of the acoustically isolating region 250. According to various non-limiting example implementations, an acoustically isolating region 250 may be formed by a region of substantial reduced mass density such as a fully evacuated chamber, a volume constructed out of thin filament webbing, a chamber constructed with stiff massive walls. Alternatively, an acoustically isolating chamber could be formed using walls made of high density material, such that the acoustic impedance mismatch between the headrest material and the wall material of the acoustically isolating chamber results in a transmission coefficient of less that 50% or less.

This example embodiment also illustrates an acoustic communication system in which acoustic communication is facilitated in the absence of sound wave propagation, whereby the vibration actuators 210 and the bone conduction microphone 240 enable acoustic communication based on the acoustic conduction of vibrations to and from the patient.

Figure 7:
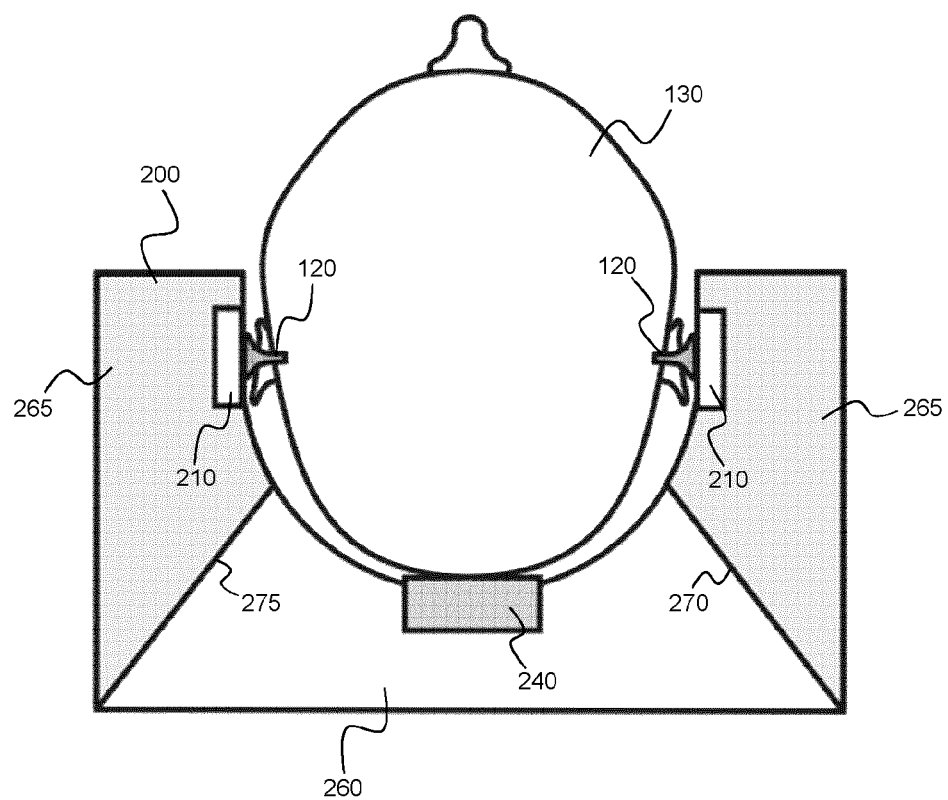
FIGS. 7-8 illustrate example communication systems in which the headrest is formed from multiple materials in order to reduce acoustic coupling between the vibration actuators and the bone conduction microphone.

Referring now to FIG. 7, an example headrest-based communication system is illustrated in which the headrest 200 includes different regions formed from different materials (the figure shows in an example implementation involving two different materials). In the example implementation shown in the figure, the headrest 200 includes a base portion 260 formed from a first material, where the base region resides behind the patient's head (e.g. in the present example, the base region supports the bone conduction microphone 140), and two lateral portions 265 that are formed from a second material, where the lateral portions 265 support the vibration actuators 210. The first material may be selected to have cushioning properties for providing patient comfort. Non-limiting examples of suitable materials include compressible foams or memory foams. The compressible foams may be selected such that they do not compress to less than 10% of their non-compressed thickness under the weight of the patient's head (are soft by firm enough to ensure that the patient's head does not touch the table). The second material may be selected to exhibit mechanical properties (e.g. rigidity and/or elasticity) that enable the vibration actuators 210 to make firm contact (e.g. contact suitable for effective acoustic conduction) with the earplugs 120 when the head 130 is supported by the base portion 260 of the headrest. Non-limiting examples include non-compressible materials.

In some example implementations, the physical properties of the two materials may be selected such that they have different acoustic impedances. For example, the materials may be selected such that the transmission coefficient of vibrational energy transferred from one material to the other is less than 50%. The different acoustic impedances would generate impedance mismatch boundaries 275 between the base portion 260 (housing the bone conduction microphone 240) and the lateral portions 265 (housing the vibrational actuators 210), such that waves travelling from the vibration actuators 210 towards the bone conduction microphone 240 would experience a reflection, thereby reducing the amount of acoustic coupling between the vibration actuators 210 and the bone conduction microphone 240.

Figure 8:
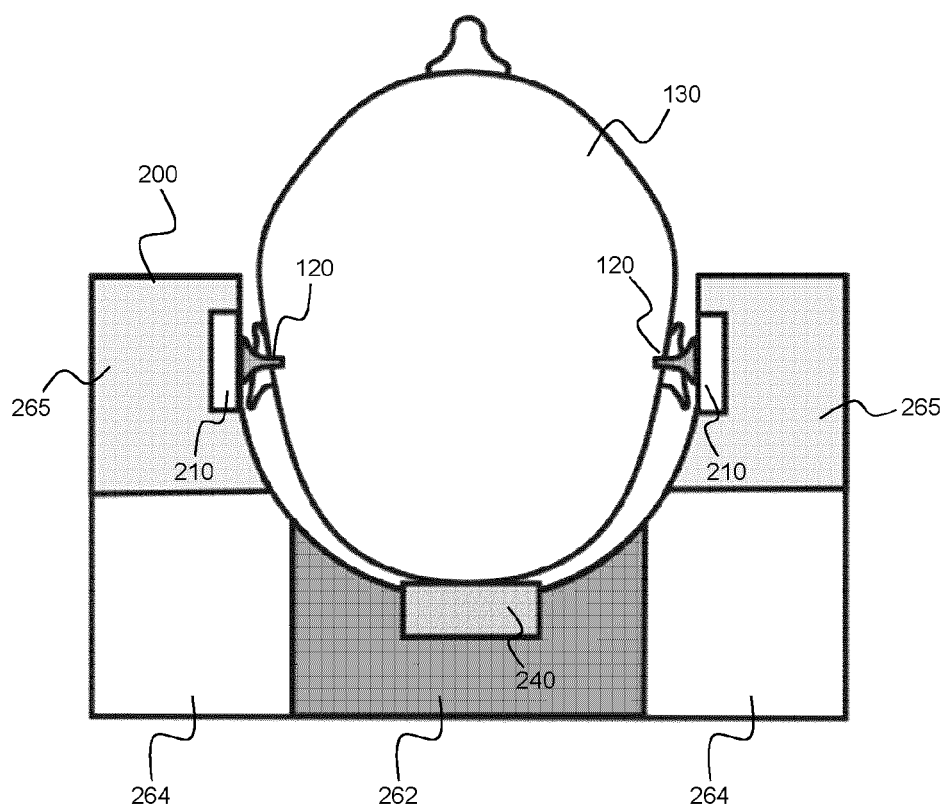

FIG. 8 illustrates another example embodiment in which the headrest 200 includes acoustically isolating regions between the vibrational actuators 210 and the bone conduction microphone 240. As in the example embodiment shown in FIG. 7, different materials may be employed in the central base region behind 262 the head and the lateral regions 265 adjacent to the patient's ears (alternatively, a common material may be used for the lateral regions 265 and the central base region 262). In the present example, acoustically isolating regions 264 are provided between the lateral regions 265 and the central base region 262, where the acoustically isolating regions 264 include a material that acoustically isolates the vibrational actuators 210 from the bone conduction microphone 240. For example, the acoustically isolating regions 264 may be formed from a very dense material such as, but not limited to, neoprene, which is selected to create an acoustic barrier in order create inefficient transmission coefficient through the boundary of less than 50%. In another example, the acoustically isolating regions may be formed from a material with an attenuation coefficient greater than −0.5 db/cm to reduce acoustic conduction between the actuators and the microphone. Non-limiting examples include a very low density parse and porous foam, an evcauated region, or a gas-filled region.

Figure 9A:
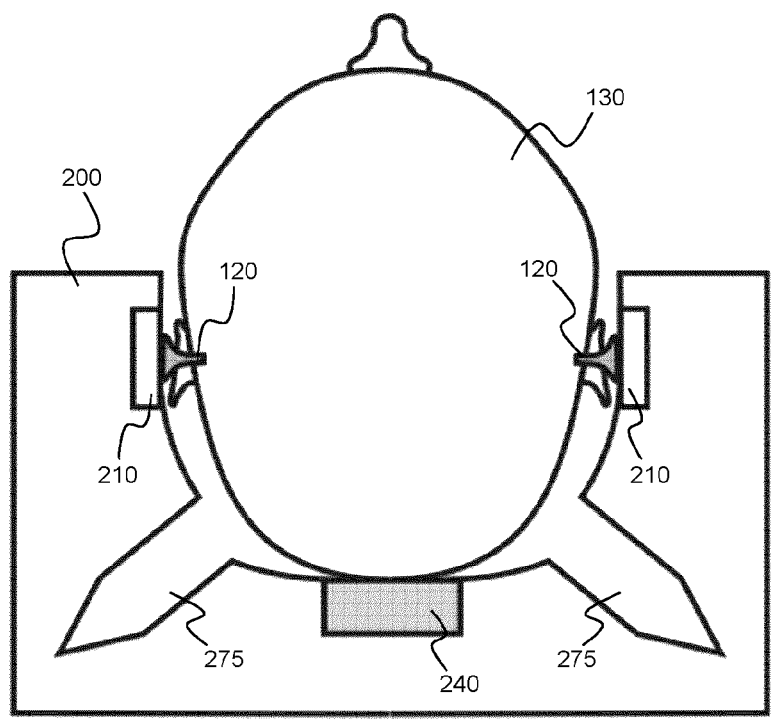
FIG. 9A illustrates an example communication system in which the headrest is formed from a material including air channels in order to reduce acoustic coupling between the vibration actuators and the bone conduction microphone.

Referring now to FIG. 9A, an example headrest-based communication system is provided in which the headrest 200 includes two acoustically isolating channels 270. The channels are located between the vibration actuators 210 and the bone conduction microphone 240, thereby reducing the amount of acoustic coupling between the vibration actuators 210 and the bone conduction microphone 240. This reduction in acoustic coupling is achieved by removing material of the headrest that would otherwise conduct vibrations from the vibration actuators 210 to the bone conduction microphone 240. It will be understood that the example implementation shown in FIG. 9A is provided to illustrate one non-limiting example of many different possible channel geometries that can be formed in the headrest in order to reduce or prevent acoustic conductive coupling between the vibration actuators 210 and the bone conduction microphone 240. Various alternative channel and cut-out configurations may be employed to increase the effective path length between the vibration actuators 210 and the bone conduction microphone 240.

Figure 9B:
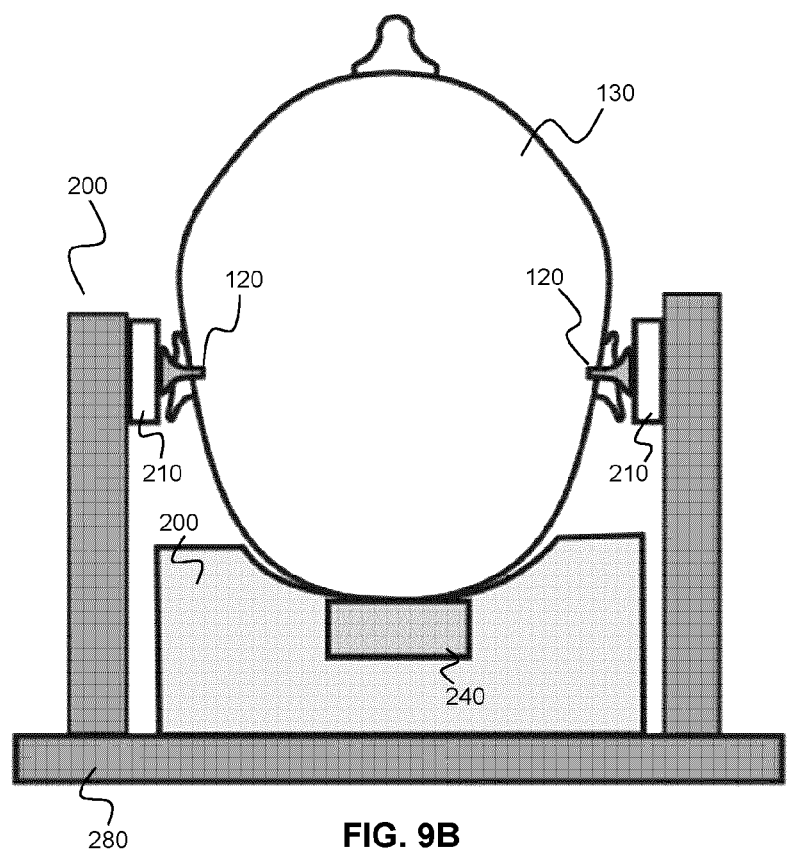
FIGS. 9B-E illustrate various different headset configurations and vibration actuator support mechanisms.

With reference to FIG. 9B, an example headrest-based communication system is shown in which the vibration actuators 210 used to contact the earplugs 120 worn by the patient are supported by a support frame 280 that is physically separated from the headrest 200 that houses the bone conduction microphone 240. Separating the vibration actuators 210 from the headrest portion 240 has the advantage of reducing coupling between the vibration actuators 210 and the bone conduction microphone 240.

In some example embodiments, one or more positioning mechanisms may be integrated into the support frame 280 to facilitate adjustment of the locations of vibration actuator 210 supports in order to accommodate a range of head sizes.

Figure 9C:
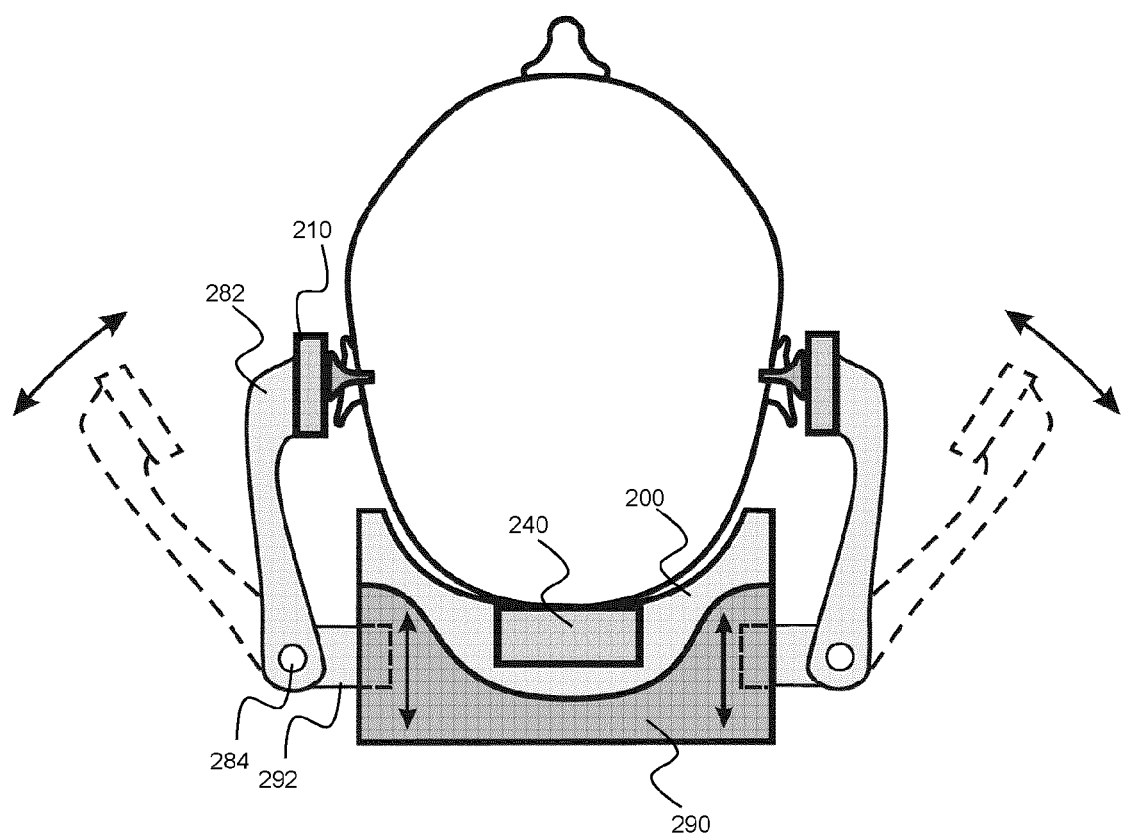

The head support and ear conduction device should be positioned with respect to the patient to ensure sufficient pressure on the earplug to maximize its occlusion of the ear canal yet not be uncomfortable to the patient. This could require some adjustment of the apparatus to adapt to different patient sizes, position and shape. Accordingly, in some example embodiments, a head support may be configured to provides mechanical structures to allow the positioning (e.g. three degrees of motional freedom) of the vibration source. As shown in FIG. 9C, the vibration source 210 may be mounted at the end of a support arm 282 which can rotated about a pivot 284. This pivot 284 could be spring loaded to maintain compression of the vibration source onto the sound attenuating earplug.

In the present example embodiment, the patient's head rests on a head support 200 made of soft memory foam which in turn supports the bone conduction cranial microphone 240. The head support 200 rests on top of an mounting frame 290, shown in cross-section. This mounting frame has attached a sliding pivot arm connector 292. This slide would be in the form of a dovetailed bevel that allows movement of the support arm and pivot in the vertical direction as shown. Thus by virtue of the vertical motion of the support to pivot arm connector 292 and the rotating motion of the support arm 282, the vibration source 210 can be accurately positioned onto the ear and attenuating earplug regardless of the patient's body habitus or head orientation.

Figure 9D:
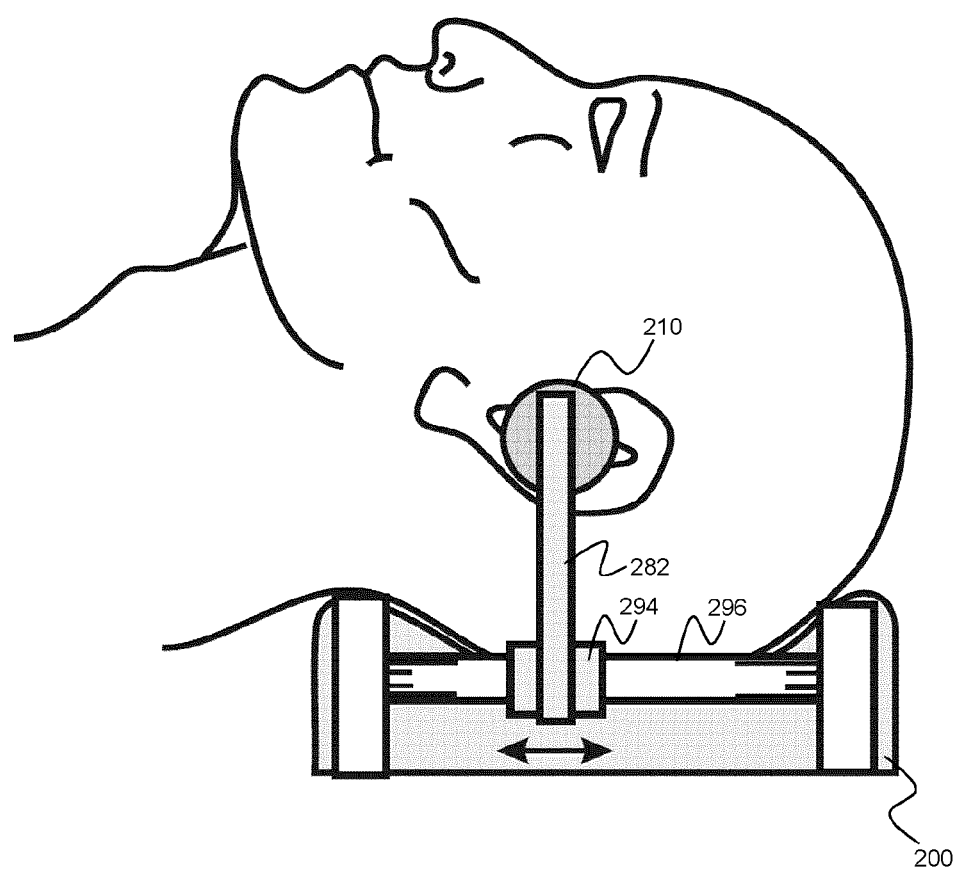

In order to conveniently accommodate the patient's position in the cranial-caudal (CC) direction, the head support 200 provides another adjustment as shown in FIG. 9D. The pivot arm runs on a linear bearing 294 which can slide over a shaft 296 and designed so as to maintain the spring loaded feature of the pivot arm loading. This permits adjustment of the vibration source 210 position of the support arm in the CC direction.

Figure 9E:
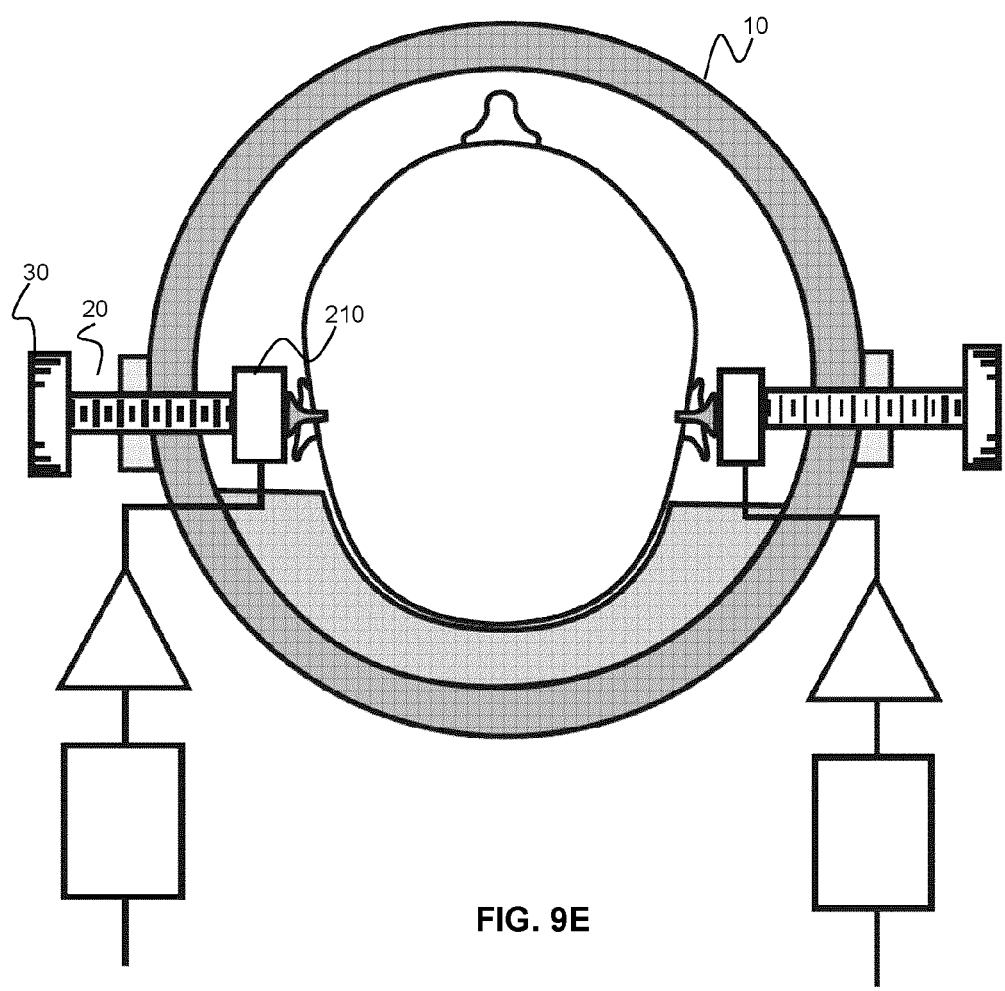

In order to ensure efficient conduction of vibration to the patient, the vibratory sources may be held in on a fixed and rigid frame, as shown in FIG. 9E. One means to achieve this would be constructed using a rigid cylinder 10 which surrounds the patient's head. The patient's head would rest on a soft head rest while the ear plugs and inserted into the ear. The vibration sources 210 would be connected to the cylinder via an adjustable connection 20 which could include a threaded rod to allow varying positions of the vibration source through the knob 30.

In some embodiments, the earplugs worn by the patient are configured to completely occlude the wearer's ear canal, such that the earplug extends across the cross section of the ear canal over a portion of the length of the ear canal, thereby providing passive noise isolation (protection) against ambient noise. The earplugs thus provide isolation from propagating sound waves (ambient noise) while facilitating physical contact (direct or indirect) with the vibration actuator in order to enable conductive acoustic communication, as described above.

Figure 10A:
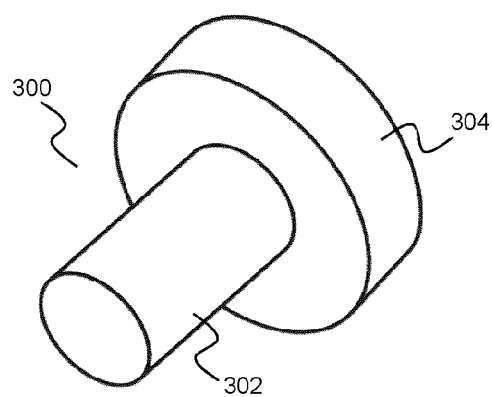
FIGS. 10A, 10B and 11-14 illustrate various example earplug configurations.

FIG. 10A illustrates an example of an earplug 300 that is configured to occlude the ear canal while providing acoustic coupling between the vibration actuators 210 and tissue of the patient. The example earplug 300 consists of a distal elongate portion 302 that is configured to be insertable into the ear canal. The distal elongate portion 302 is formed from a compressible material, such that when the distal elongate portion 302 is inserted into the ear canal, the distal elongate portion 302 completely occludes the ear canal over at least a portion of the ear canal, while providing passive noise protection and facilitating acoustic conductive coupling with bony structures surrounding or adjacent to the ear canal. The distal elongate portion 302 may be cylindrical as shown in the figure, or may be provided with other shapes, provided that the shape is suitable for occlusion of the ear canal upon insertion of the distal elongate portion 302 into the ear canal. In one example embodiment, the distal elongate portion 302 of the earplug is formed from viscoelastic polyurethane foam.

The example earplug 300 also includes of a proximal acoustic coupling portion 304 configured to extend outwards from the wearer's ear when the distal elongate portion 302 is inserted into the ear canal. The proximal acoustic coupling portion 304 extends outward in order to make contact with the headrest 200 or the vibration actuator 120, such that vibrations generated by the vibration actuator 120 are acoustically conducted through the earplug 300 and into the bony tissues surrounding the ear canal. The proximal acoustic coupling portion 304 may be formed from the same material as the distal elongate portion, such as viscoelastic polyurethane foam. Alternatively, the proximal acoustic coupling portion may 304 may be formed from a material having one or more different properties than the distal elongate portion 302.

In some example implementations, the earplug 300 may be formed as a monolithic structure, or by joining the distal elongate portion 302 to the proximal acoustic coupling portion 304.

In some example embodiments, the earplug 300 may be formed from an electrically conductive material. In such a case, if the contact point with the headrest 200 and/or vibration actuator 210 is also electrically conductive, the conductive pathway (or pathways, if both earplugs are conductive) to the subject may facilitate detection of when suitable contact has been established. In an alternative example embodiment, the headrest 200 may include one or more pressure sensors configured to determine whether or not sufficient pressure between the headrest 200 and the earbud has been established during use.

Figure 10B:
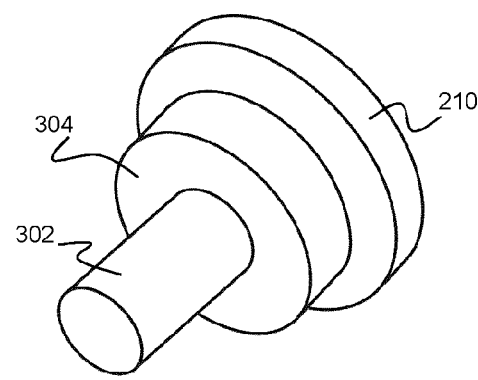

The proximal acoustic coupling portion 304, while shown in FIG. 10 as a cylindrical disc (e.g. a proximal acoustic coupling flange), may be provided with a wide variety of shapes, provided that the proximal acoustic coupling portion 304 is capable of making contact with the headrest 200 and/or vibration actuator 210 when the distal elongate portion 302 is inserted into the ear canal.

FIG. 10A illustrates the example earplug of FIG. 10A contacted with an example cylindrical vibration actuator 210.

Figure 11:
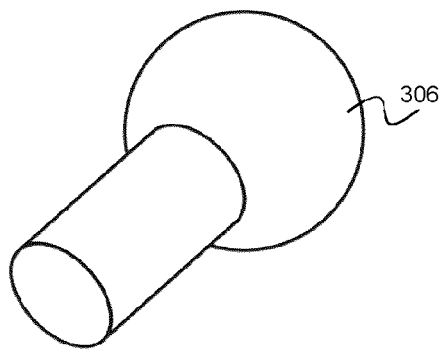

For example, as illustrated in FIG. 11, the proximal acoustic coupling portion may be spherical (or hemispherical) in shape, as shown at 306.

Figure 12:
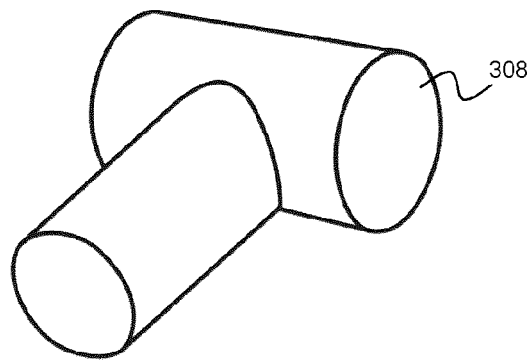

In another example embodiment, the proximal acoustic coupling portion 304 may be provided with an elongate shape having a longitudinal axis angled relative to a longitudinal axis of the distal elongate portion 302. For example, as shown in FIG. 12, the proximal acoustic coupling portion may be provided in the form of a cylindrical shape, as shown at 308, where a longitudinal axis of the cylindrical acoustic coupling portion 308 is orthogonal to a longitudinal axis of the distal elongate portion 302.

Figure 13:
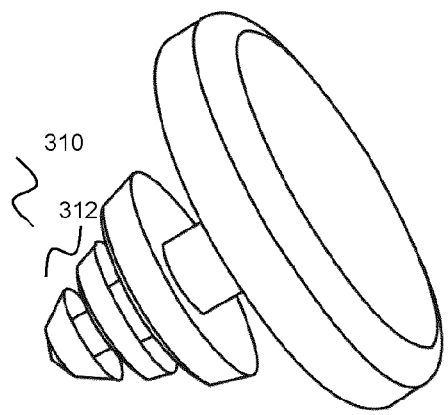

It will be apparent to the skilled artisan that many alternative shapes may be employed for the proximal acoustic coupling portion and the distal elongate portion. For example, the distal elongate portion of the earplug may include a plurality of occluding structures. The occluding structures may extend radially from a central elongate member. FIG. 13 illustrates an example implementation in which the distal elongate portion includes a plurality of occluding discs 310 spaced longitudinally along, and extending in a radial direction from, a distal elongate member 312. The occluding discs 310 facilitate occlusion of the ear canal, mechanically support the earplug within the ear canal, and facilitate acoustic coupling to the tissue structures surrounding the ear canal.

In some example implementations, the distal elongate portion and the proximal acoustic coupling portion of the earplug may be formed from a common material. Alternatively, the distal elongate portion and the proximal acoustic coupling portion may be formed from multiple materials to improve the functionality of the earplug. In some example implementations, one or both of the distal elongate portion and the proximal acoustic coupling portion may be made from multiple materials.

Figure 14:
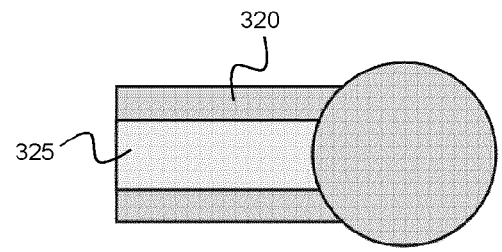

FIG. 14 illustrates an example earplug that is made using two different materials, showing a cross-sectional view, where the first material forms a peripheral region 320 of the earplug and facilitates efficient coupling of vibrations from the earplug onto tissues. This first material may be selected to exhibit a density that is similar (e.g. within the same order of magnitude; e.g. within 10×) to that of the tissues that surround the ear canal and temporal bone, in order to facilitate efficient acoustic coupling from the earplug to tissues surrounding the ear canal. However, in order to provide sufficient compressibility of the earplug for convenient insertion and to maintain sufficient contact between the first material and the tissue, a second material may be employed to form a central (e.g. core) region 325 of the earplug. This second material may be provided with a lower density, while exhibiting higher compressibility and/or elasticity than the first material. An example of a desirable material includes but is not limited to a semi-compressible foam. The purpose of the semi-compressible foam is to apply pressure to the ear canal to increase the friction between the first material and the ear canal thereby increasing the transmission of vibrations from the earplug to the temporal bone. The core material can also be selected to provide noise isolation, while the peripheral portion provides acoustic coupling between the temporal bone and the vibration actuator.

An alternative to actuation of sound via bone conduction would be insert a device similar to a balloon catheter into the ear canal as shown in FIG. 1. At the tip of the catheter is an expandable balloon composed of a material such as flexible rubber, which could alternatively be made of other materials such as latex. In its native state the balloon is collapsed and small enough to be inserted into the ear canal. By using a syringe or similar pressure inducing device, a fluid, such as sterile water, could be pumped into the balloon via the tube. This would serve to inflate the balloon with sterile water and thereby occlude the ear canal as a passive noise reduction system.

Accordingly, in some example embodiments, at least a portion of the earplug may filled with an incompressible liquid that provides noise isolating occlusion of the ear canal while also providing acoustic coupling for conducting vibrations from the vibration actuators to the tissues surrounding the ear canal. For example, as shown in FIGS. 15A and 15B, an earplug assembly is illustrated that includes a flexible catheter having an elongate sheath defining at least one lumen 350, where the lumen 350 is in fluid communication an inflatable balloon 360 located at or near a distal end of the elongate sheath. The proximal end of the catheter is connected or connectable to a syringe 370 or other device that is capable of increasing the pressure within the balloon 360 to inflate the balloon.

As shown in FIGS. 15C and 15D, the distal portion of the elongate sheath may be inserted into the ear canal with the balloon 360 initially in an uninflated state. Upon injection of fluid into the lumen 350 under the application of pressure by the syringe 370, the balloon fills 360 with the fluid and is inflated, such that an outer surface of the balloon 360 makes contact with the inner surface of the ear canal. The fluid used to fill the balloon may be, but is not limited to, fluids such as water, saline, and mineral oil. The fluid-filled balloon 360 provides passive noise isolation by virtue of filling the ear canal with a dense material and having a seal with the ear canal. The distal portion of the elongate sheath may be configured such that the lumen expands towards and/or within the balloon 360, thereby reducing acoustic reflections.

The catheter portion may be formed from materials such as, but not limited to, PEEBAX, silicone rubber, nylon, polyurethane, polyethylene terephthalate (PET), latex, and thermoplastic elastomers. The balloon portion 360 of the device could be constructed using materials similar to those employed in the fabrication of angioplasty balloons. Non-limiting examples include flexible PVC (polyvinyl chloride), polyethylene terephthalate (PET), and nylon.

Figure 16A:
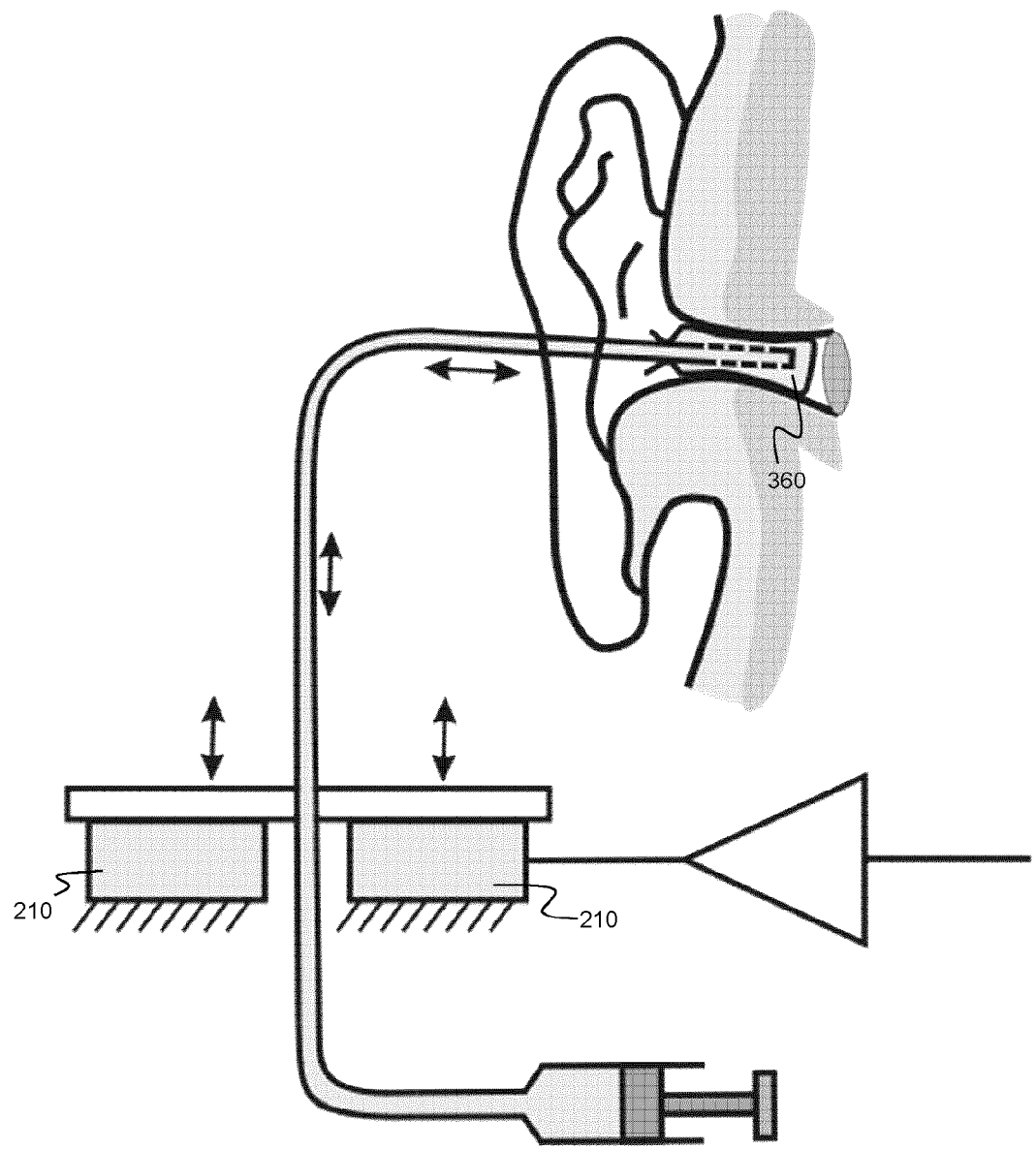
FIGS. 16A-B illustrate various example embodiments in which a fluid filled catheter is employed to acoustically couple a vibration actuator to a fluid-filled balloon expanded within the ear canal.

FIG. 16A illustrates an example communication device utilizing the balloon catheter earplug of FIGS. 15A-D. As shown in FIG. 16, a portion of the catheter is contacted with one or more vibration actuation devices 210. This contact produces vibrations that travel along the catheter towards to distal balloon 360. The patient hearing is enabled through the production of vibrations that are directed into the earplug using one or more vibration actuators 210 that is located away from the earplug device that makes contact with the fluid filled catheter. The bottom side of the vibration actuators are illustrated as being fixed to a non-moving mass such that all of their vibrational energy is transferred to the catheter.

In an alternative example embodiment, the plunger of the syringe shown in FIG. 16A may be adapted to include an acoustic generating element, such as a speaker diaphragm or a piezoelectric transducer, thereby enabling the direct excitation of longitudinal sound waves within the lumen of the elongate sheath.

Figure 16B:
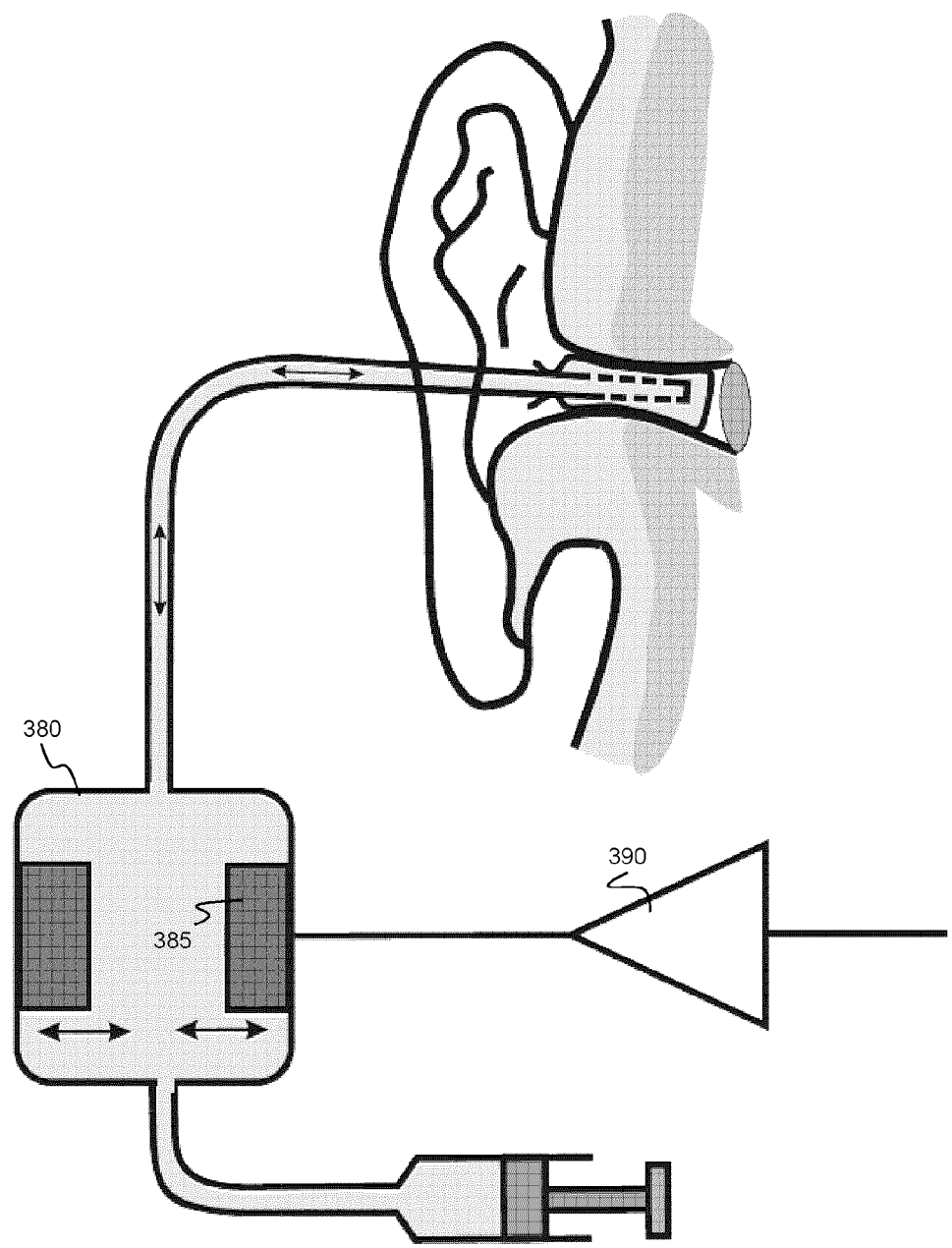

FIG. 16B illustrates an alternative example embodiment in which the catheter conduit passes into a rigid, water tight chamber 380 which contains electro-mechanical actuators 380. The actuators could be composed of a piezoelectric material such that under electrical stimulation the actuators would undergo expansion. The actuators would be powered through an audio amplifier 390 which connects the actuators through the chamber. As the audio signals from this amplifier causes expansion and contraction of the actuators, the fluid surrounding the actuator will undergo oscillator pressure changes which is conducted along the conduit to the ear canal and balloon. This will cause the balloon to experience vibratory oscillations which will be conducted into the patient's auditory system via bone conduction or the tympanic membrane.

In the preceding example embodiments, the vibration actuators were described as being located within or on a headrest that supports the patient's head, such that the vibration actuators are brought into acoustic contact with passive earplugs worn by the patient. The following alternative example embodiments pertain to active earplugs that have integrated vibration actuators.

Figure 17:
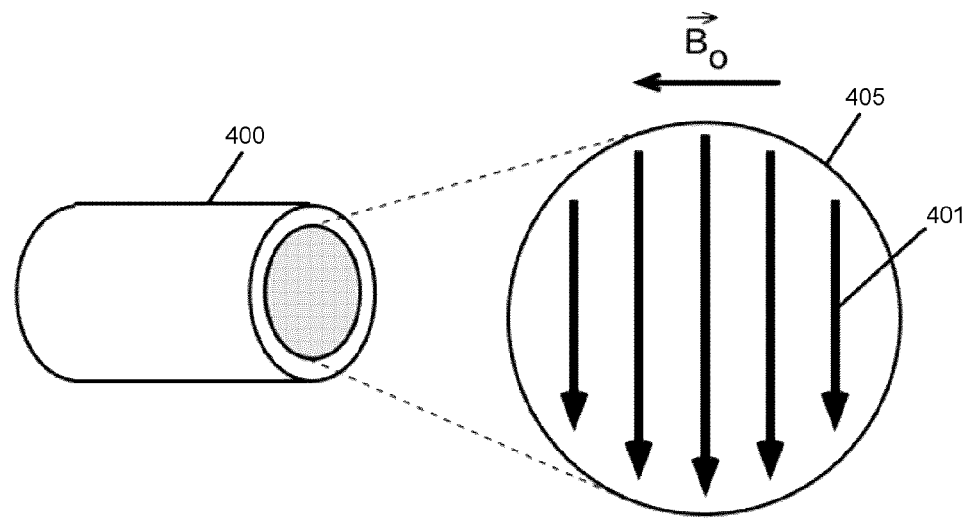
FIGS. 17-22 illustrate various example implementations of a Lorentz-based vibration transducer.

With reference to FIG. 17, an example embodiment of an active earbud is shown, where a foam earplug 400 is illustrated having a substrate 405 attached or adhered thereto, where the substrate 405 contains one or more conductors (e.g. conductive paths or traces) that act as a Lorentz vibration actuator. A current I flows within each of the conductors in the direction as indicated by the arrows 401 in the figure. The circular substrate 405 is positioned so that the conductors are directed at an angle (preferably perpendicular) relative to the main static magnetic field $B_0$ of the MRI scanner when the active earplugs are worn by the patient. The conductors 410 each experience a Lorentz force F in the direction perpendicular to both the static magnetic field $B_0$ and the current according the equation:

$$F = I \int dl \times B_0 \qquad (1)$$

The Lorentz force that acts on the conductors 410 causes a displacement of the substrate. When an alternating current is applied to the traces at audio frequencies, the substrate is responsively displaced at the same frequency, thereby generating a propagating pressure wave. This pressure wave is conducted through the earplug due to the contact between the substrate and the earplug, and onto the bones surrounding the ear canal, such that the pressure wave produces audible sound that is perceived by the wearer of the earplugs.

As noted above, the conductive traces need not be oriented perpendicular to the static magnetic field of the MRI scanner. In the event that the earplugs are worn such that the conductors are not perpendicular to the main static field of the MRI scanner, the component of the current on the conductive traces in a direction perpendicular to the magnetic field will cause displacement of the substrate.

It should be noted that the substrate on which the conductors are attached does need not be rigid, and could be a flexible substrate made out of materials including, but are not limited to, polyimide (Kapton), plastic, and any type of flexible polymer, provided that the substrate is attached, adhered, affixed, pressed against or otherwise mechanically contacted with the earplug, so that vibrations originating from the substrate are able to be transmitted onto the earplug.

In one example implementation, the substrate and conductive traces may be formed use of a flexible printed circuit board, where the a suitable conductor pattern is etched onto a sheet a copper clad laminate. Alternatively, in an alternative example implementation, the conductors could be directly affixed to the earplug, in the absence of an intervening substrate.

Figure 18:
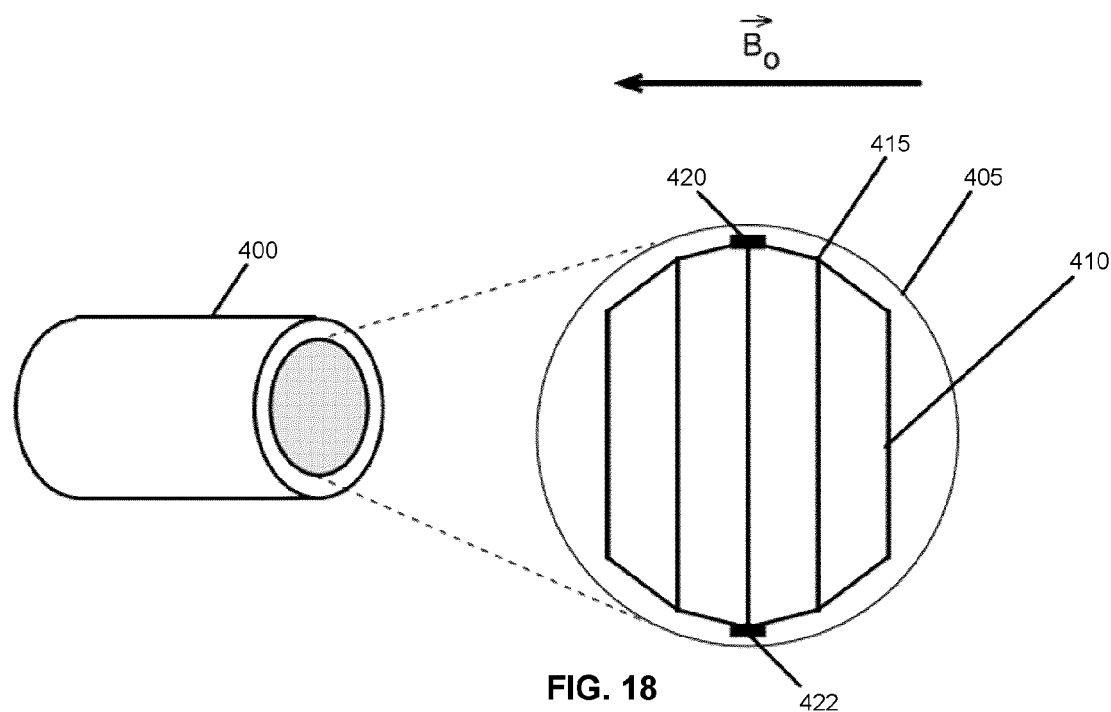

FIG. 18 illustrates an example implementation in which the conductive traces 410 that are oriented such that when the earplug is worn by a patient within a magnetic resonance scanner, the conductive traces 410 are are directed at an angle (preferably perpendicular) relative to the static field of the MRI scanner (the Bo field). The conductive traces 410 are connected in parallel, as shown in the figure, by segments 415. When an alternating voltage is applied to the terminals (420 and 422) located at either ends of the conductive traces 415, current flows through the conductive traces. The Lorentz force applied to the conductive traces 410 causes displacement of the substrate 405, thereby creating a pressure wave that will be hear by the wearer through bone conduction. The conductive traces 415 could consist of any suitable conductive material. Examples include, but are not limited to copper, tin, silver, or gold.

Figure 19:
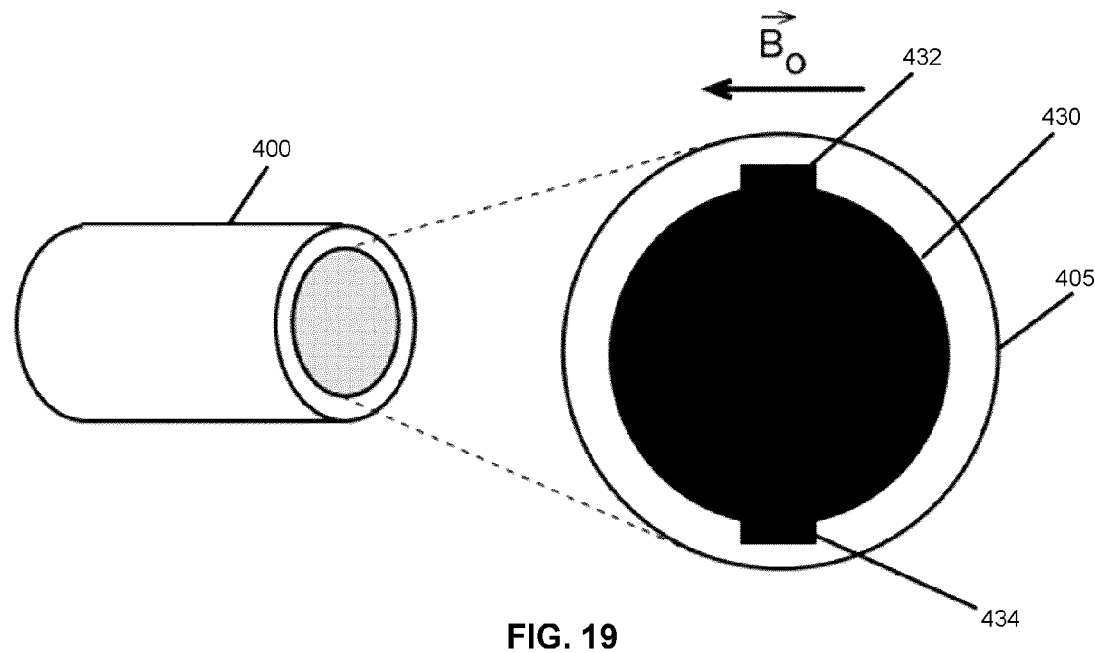

With reference to FIG. 19, an example embodiment of an active earplug 400 is illustrated with an attached conductor consisting of a solid planar segment of conductive material 430. Two electrodes (432 and 434) are located on either side of the conductive plane. Current flowing between the two electrodes is distributed across the plane thereby also creating a distributed Lorentz force on the conductive place.

Figure 20:
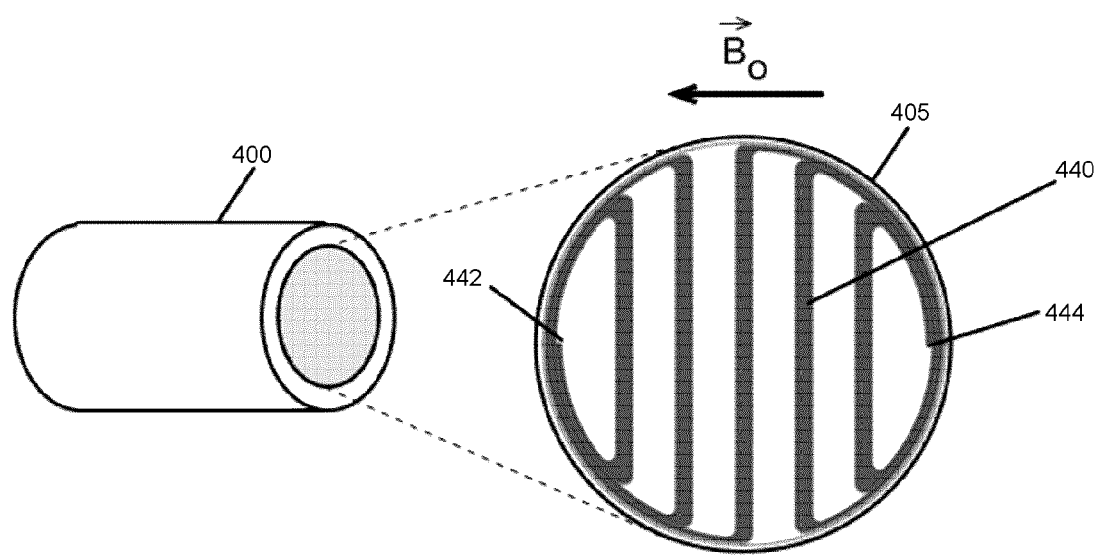

With reference to FIG. 20, an example embodiment of an active earplug 400 is illustrated, in which a series of with vertical conductive traces 440 affixed to the flexible membrane are connected to each other in series (as opposed to in parallel as illustrated in FIG. 18). Additional conductors, shown at 442 and 444, are present to connect the conductive traces so that the current in conductor traces flows in the same direction in all of the vertical traces, so that the Lorentz force created on the vertical traces is in the same direction on the face of the substrate. The additional conductive traces connecting the vertical traces are purposely placed on the perimeter of the substrate. Despite there being regions on the perimeter conductors where the Lorentz force is opposite to that of the vertical conductors, an overall net Lorentz force on the substrate would still be present. If a flexible substrate is used, the Lorentz force distribution may one cause a characteristic bending of the substrate. Overall, vibrations are still created and are conducted through the earplug material. An advantage of having the vertical traces connected in series is that less current at the terminals is needed to create the equivalent Lorentz forces over the surface of the substrate. In this example, the additional conductors connecting the central vertical traces 440 are illustrated as additional traces affixed to the substrate (such as those that would be present on a printed flexible circuit), but it will be understood that these additional conductors could alternatively be provided in the form of magnet wire, insulated copper wire, or any other type of conductor.

It should be understood that the conductive traces in FIG. 18 and FIG. 20 are illustrated as vertical traces for the purposes of simplicity because the traces are perpendicular to the main static field of the MRI ($B_o$). However, it will be understood by those skilled in the art that in order for a Lorentz force to be created on the conductor, the current vector associated with conductive trace needs to only have a component that is perpendicular to the magnetic field. Alternative example embodiments could employ several conductor trace patterns resulting in a Lorentz force that would cause displacement on the substrate, thereby creating sound.

Figure 21:
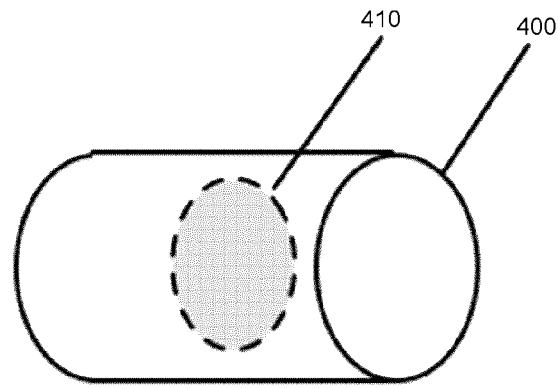

It the preceding figures, the conductors have been illustrated as being located on an outside face of the earplug. With reference to FIG. 21, an earplug is illustrated with the conductors 410 embedded inside the earplug 400, instead of on an outer surface of the earplug 400.

The example embodiments shown in FIGS. 18-20 have been described as being capable of generating sound that can be heard by the wearer via bone conduction. However, active components shown in in FIGS. 18-20 can additionally or alternatively be employed to sense vibrations produced by the wearer of the earplug during speech.

Figure 22:
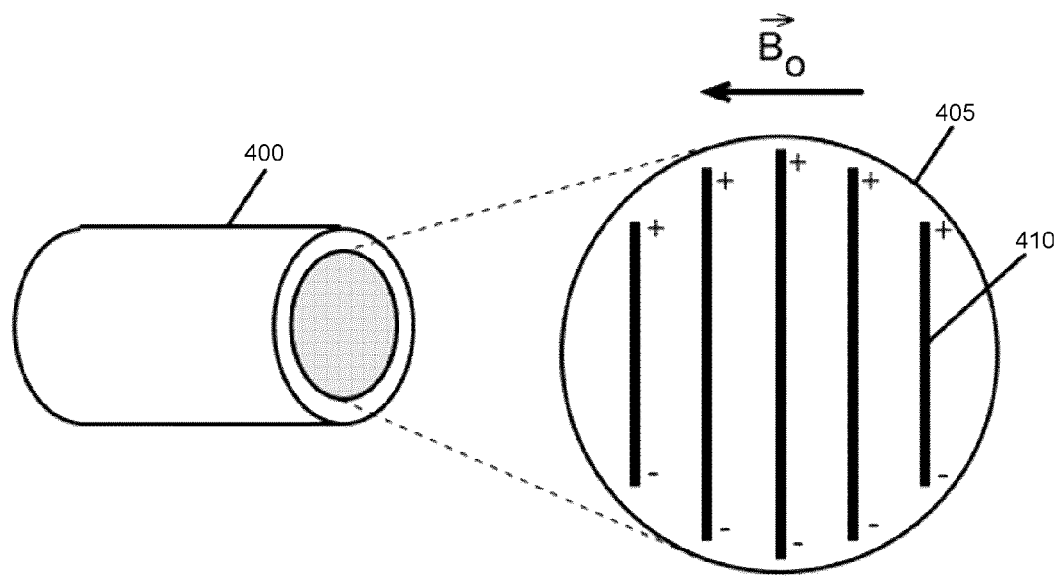

During speech, vibrations originating at the vocal cords are transferred to bony structures including bones located long the ear canal. With reference to FIG. 22, an active earplug 400 is illustrated that incorporates with a series of vertical conductors 410 on a substrate 405. During speech, the wearer induces small vibrations on the earplug 400 that causes the substrate, and the conductors 410 formed thereon, to also vibrate. A voltage V will be induced across each conductor 410, where the voltage is proportional to the component of the velocity v of the conductor in the direction that is perpendicular to the main static field of the MRI ($B_o$) according to the equation:

$$V = v \int dl \times B_o. \tag{2}$$

The time-varying voltage across the conductors 410 is directly proportional to the amplitude of vibrations and is representative of speech. As such, the device can be used as a microphone and used as an input to a recording or audio communication system.

It should be understood that several types of conductor configurations are possible for forming a microphone on an earplug. These include but are not limited to those illustrated in FIGS. 18-20.

The microphone configurations provided according to the present disclosure have several advantages for use in the MRI environment. Because, speech sensing is performed based on vibrations, the device is inherently insensitive to ambient noise. As such it will not be sensitive to the loud noises of the MRI scanner and will enable effective communication during the operation of the MRI scanner. It should be noted again, that while the conductors are illustrated as being attached to a face of the earplug in FIGS. 18-20, the conductors may alternatively be embedded within the earplug, as illustrated in FIG. 21.

Figure 23:
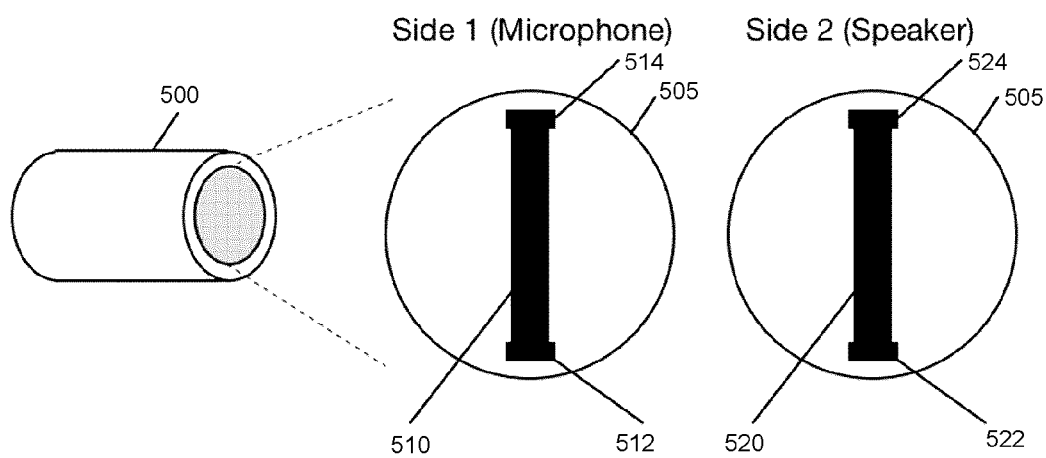

With reference to FIG. 23, an example embodiment of an active earplug 500 for two-way communication is illustrated. A substrate 505 is attached to the earplug 500, where the substrate 405 has conductors 510 and 520 present of both sides of the substrate to form an earplug with a combined microphone and speaker. Two pairs of electrodes (512, 514 and 522, 524, respectively) are placed on the ends of each conductor on the two sides of the substrate 505. The electrodes 510 on one side of the substrate form the output of a microphone and the electrodes on the other side of the substrate form the input to a speaker 520. It is again noted that although the conductors are illustrated as single traces for simplicity, their configurations could be more complex as described above. In addition, it will be understood that the substrate does not necessarily need to be attached to the outside face of the earplug but could rather also be embedded inside the earplug.

In one example embodiment, the geometric relationship of the conductors used for a microphone and for a speaker to can be employed to decouple their operation. During normal operation, current input into the speaker electrodes 522, 524 could cause vibrations of the speaker conductors 520. Since the microphone conductors 510 are attached to the same substrate 505 as the speaker conductors 520, the vibration of the speaker conductors 520 would cause displacement of the microphone conductors 510. This displacement would cause an unwanted voltage to be present at the microphone electrodes 512, 514. To state this more clearly, the microphone and speaker are highly coupled as the intended input to the speaker would induce an output on the microphone.

The coupling can however be removed through use of equations 1 and 2 above. Using equations 1, the force exerted on the speaker conductors 520 and the microphone conductors 510 can be calculated for a generic time-varying speaker input. Using knowledge of properties of the earplug material, such as its elasticity and stiffness, these forces can be converted into a displacement. This known displacement enables the determination of the velocity of the microphone conductors 510 and hence an estimate of the expected output signal that would be present on the microphone electrodes 510. This calculated output signal can then be removed from the microphone signal.

Figure 24:
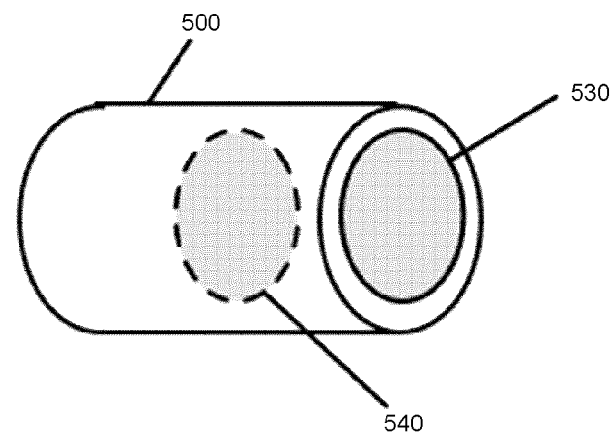

With reference to FIG. 24, the microphone and speaker conductors are shown as being provided on different substrates 540 and 540, where the two substrates are positioned at different locations on or within the earplug 500, including one or both being embedded inside the earplug. It other example embodiments, the speaker conductors or the microphone conductors may be formed directly on a proximal outer surface of the earplug (a surface facing outwards away from the head).

Figure 25:
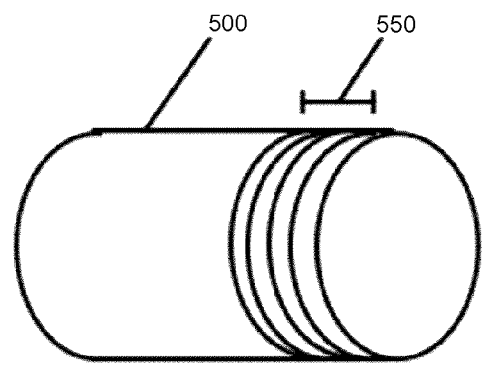

With reference to FIG. 25, an example embodiment of a cylindrical earplug 500 is illustrated that incorporates a multi-turn coiled conductor 550 wrapped around the outside of the earplug 500. The vibrations induced by speech in the earplug 500 (via bone conduction) will have a rotational component that will cause the angle between the axis of the coiled conductor and the static magnetic field to oscillate. This will cause a change in magnetic flux through the coiled conductor loop 550, which will result in a voltage being present at the leads of the coiled conductor 550 that is representative of speech. The earplug 500 containing the coiled conductor 550 can therefore be used as a microphone. As in the microphone embodiments described above, this example embodiment is also insensitive to ambient noise such as that produced by the operation of the MRI scanner, due to the noise isolation provided by the distal and insertable portion of the earplug 500 that occludes the ear canal over at least a portion of its length. The coiled conductor can be formed from materials including, but not limited, to insulated copper wire and other conductive wires. In addition, it will be understood that while the coil conductor 550 shown in FIG. 25 is illustrated as being wrapped around the outside surface of the earplug, the coiled conductor may alternatively be embedded within the earplug.

Figure 26A:
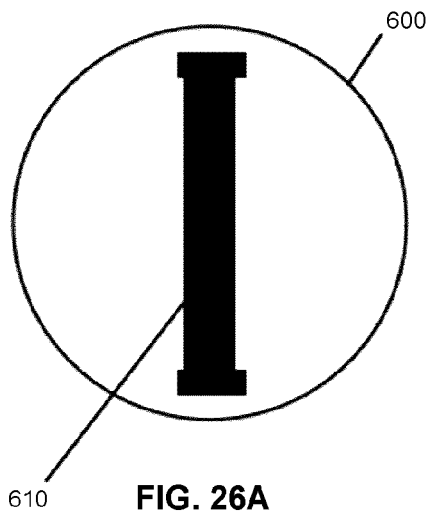
Figure 26B:
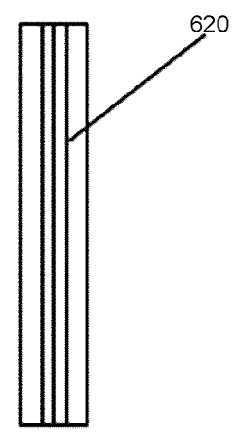

With reference to FIG. 26, an example embodiment of a rigid substrate 600 for attachment and use with a noise-isolating earplug is illustrated. The rigid substrate 600 includes a planar conductor 610 that operates as a vibrational speaker as described above when placed within a static magnetic field. A coiled conductor 620 is located around the edge of the substrate 600 and can be used as a microphone. When attached to, or embedded within an earplug, the present rigid substrate can be employed for bi-directional communication, acting as both a vibrational microphone and speaker in the static magnetic field of the MRI scanner. An advantage of this example embodiment is that there is inherent decoupling between the microphone and speaker. The planar conductor 610, when used as a speaker, will only create linear translations. The coiled conductor 620, when used as a microphone, is only sensitive to vibrations with a rotational component and as such the speaker and the microphone will be inherently decoupled. It should also be understood that in another example implementation, the designation and use of the speaker and microphone may be reversed, such that the coiled conductor 620 is used as a speaker and the planar conductor 610 is used as a microphone.

Figure 27:
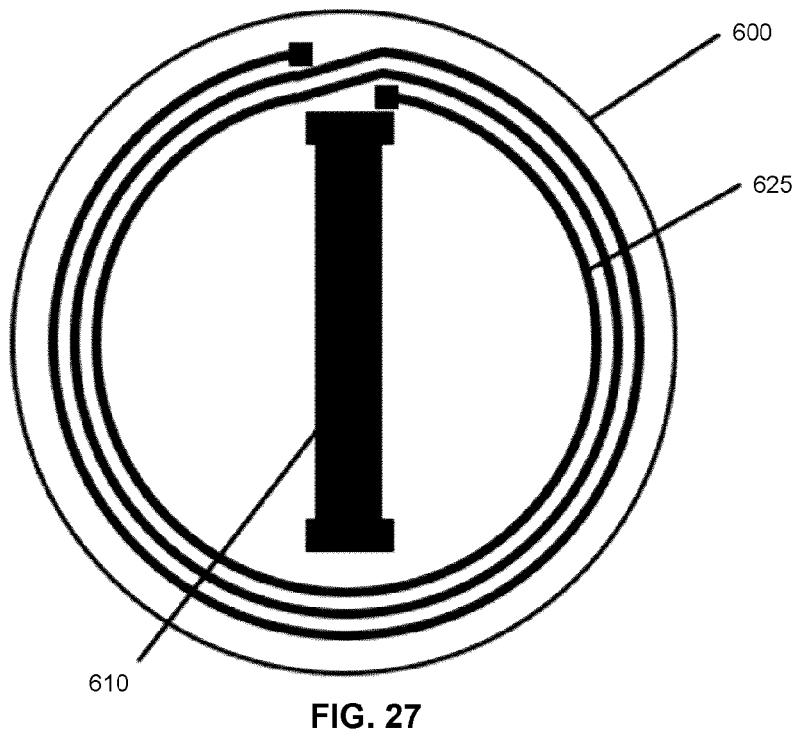

FIG. 27 illustrates and alternative example embodiment in which the coiled conductor is implemented as a planar coil that is provided on a surface of the substrate 600. In the example embodiment shown in FIG. 27, the planar coiled conductor 625 is provided on same planar surface as the speaker conductor 610. The operation of such a configuration is identical to that of previous embodiments but has the advantage that it can be fabricated out of an single-sided circuit board.

It should be noted that the location of the planar coiled conductor is not limited to the perimeter region of the substrate as is illustrated in FIG. 27. The planar coiled conductor may be placed in an any suitable location. In one example implementation, the planar coiled conductor 625 may be located on the opposite side of the substrate 600 (i.e. opposite from the face of the substrate on which the speaker conductor 610 is located).

FIG. 28 illustrates an example embodiment in which a cylindrical earplug 500 is provided with a substrate 600 attached thereto, where the substrate 600 includes a conductor 620 (having terminals 612 and 614) for use as a vibration speaker. Also affixed the substrate 600 on the opposite side is a vibration sensor 650 that is capable of outputting a voltage that is proportional to the level of vibration experienced by the sensor 650. The vibration sensor 650 may be capable of operating outside of the main static magnetic field $B_o$ of the MRI scanner, and could consist of, but is not limited to, a piezoelectric crystal, piezoelectric bender, or an accelerometer. Such a sensor may be capable of sensing vibration in a single discrete direction, or in multiple orthogonal directions. The sensor may also be omnidirectional in sensitivity.

In other example implementations, the sensor 650 may be mounted on the same face as the vibration speaker conductor 610. In the case where the sensor element is an accelerometer that is sensitive to accelerations in a single direction, the accelerometer can be mounted so that its direction of sensitivity is orthogonal to the vibrations produced by the vibration speaker. As such, the speaker and accelerometer are may be decoupled so that the accelerometer is only sensitive to vibrations produced by the wearer through speech. In example embodiments in which the accelerometer is sensitive to vibrations in three orthogonal directions and is mounted such that two of the directions of sensitivity are orthogonal to the vibrations produced by the vibration speaker, both accelerometer measurements will be decoupled from the vibration speaker, and can be combined to produce a signal representative of speech. Examples of methods for combining the measurements include, but are not limited to, linear or sum-of-squares addition.

In another example embodiment, the accelerometer may be employed as a vibration sensor that is sensitive to accelerations in three orthogonal directions. This configuration can provide additional flexibility in that the accelerometer can be mounted in an arbitrary orientation on a substrate with a vibration speaker. Due to the arbitrary or mounting of the accelerometer, it can be expected that substrate vibrations created by the operation of the vibration speaker will cause signals from the accelerometer in all three dimensions. The speaker signal can be removed by identifying the vector direction associated with the vibration speaker through an analysis of the measured signals from the accelerometer in three directions. For example, a basis transformation can be performed on the measured acceleration vector and the vector component associated with that of the vibrational speaker can removed from the measurement.

It should also be noted that the vibration sensor 650 described above does not need to be fixed to the substrate 600, and can instead be embedded in the earplug. With reference to FIG. 29, an example embodiment is shown in which an earplug 500 includes a substrate 600 having vibrational speaker located on an outside face of the earplug 500, and a vibrational microphone sensor 650 embedded within the earplug 500.

Figure 30A:
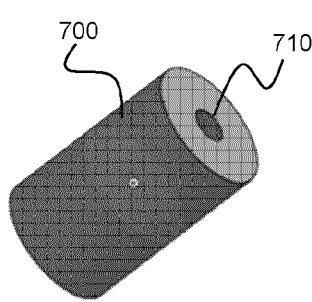
FIGS. 30A-C, 31 and 32 illustrate example embodiments in which one or more acoustic transducers are provided within a housing that is acoustically coupled to a noise isolating earplug.
Figure 30B:
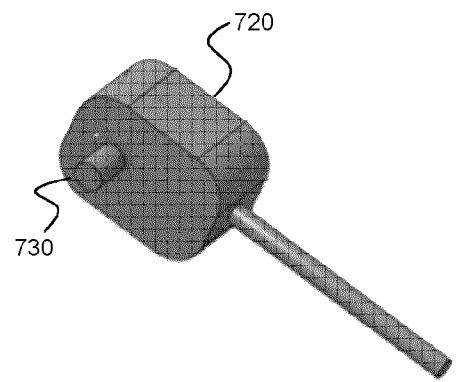
Figure 30C:
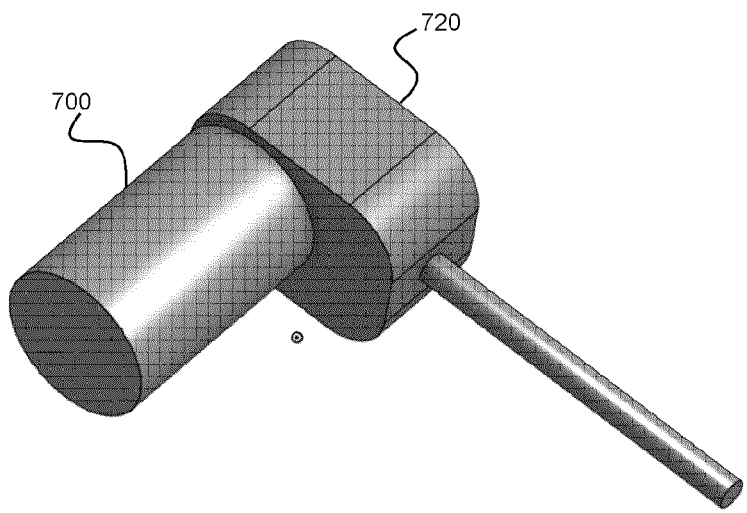

While the previous embodiments disclosure earplugs with attached or embedded conductors and sensors, other embodiments may be provided that employ removable enclosures that contain the conductors or sensors. With reference to FIGS. 30A-C, an noise isolating earplug 700 that is configured for occlusion of the ear canal upon insertion therein is illustrated with a channel (e.g. hole, aperture) 710 designed such that the earplug 700 mates securely to an enclosure 720 that contains one or more acoustic transducers (such as, but not limited to, those described above). The enclosure 720 includes distal protrusion 730 that is received within the channel 710, such that vibrations produced from an acoustic transducer housed inside the enclosure are able to effectively propagate to the earplug and subsequently to the wearers bone, and/or such that vibrations generated via speech are conducted through the earplug and into the housing, where they are detected by the acoustic transducer—i.e. the earplug and the acoustic transducer are in acoustic conductive communication.

The vibration actuators in the proceeding example are not limited to the use of Lorentz mechanisms. With reference to FIG. 30, another type of vibration actuator could be placed in the enclosure such to not utilize the static magnetic field of the MRI. Such example embodiments can therefore be used in non-MRI applications. Non-limiting examples of such devices include piezoelectric transducers, piezoelectric benders, and conventional magnetic speakers. As described above, the enclosure 720 should be mechanically coupled to the vibration actuator such that vibrations from the actuator are transferred onto the enclosure 720 and subsequently onto the earplug 700.

Figure 31:
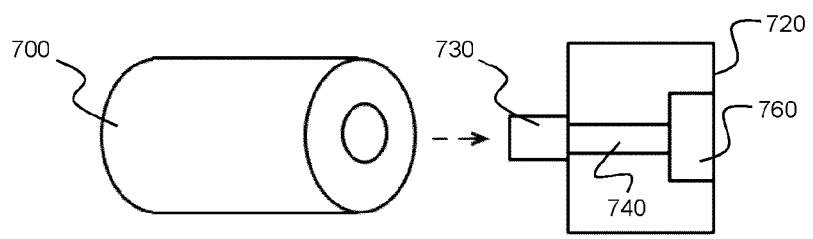

With reference to FIG. 31, a cross-section of an example enclosure is illustrated with protruding section 730 that is designed to mate with an earplug that completely occludes the ear canal. Inside the enclosure, a vibration actuator 760 is illustrated where one side of the actuator is adhered and fixed to the inside surface of the enclosure 720. An acoustic conduit 740 (e.g. a pillar or other component) of acoustically conducting material is connects the non-fixed side of the vibrational element to the protrusion 730 in order to facilitate the acoustic conduction of vibrational energy from the vibration actuator to the protruding section 730 that mates with the earplug.

Figure 32:
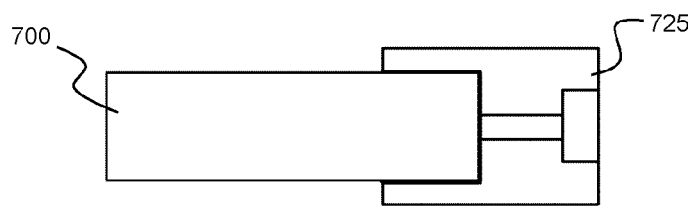

In the preceding example, it should be understood that there are multiple possible configurations with which one could mate the earplug and the enclosure. It is desirable to have a mating surface that is as large as possible to facilitate the conduction of vibrations between the enclosure and the earplug. With reference to FIG. 32, other possible embodiments include enclosure 725 that surrounds and clamps to the protruding portion of the earplug.

Figure 33:
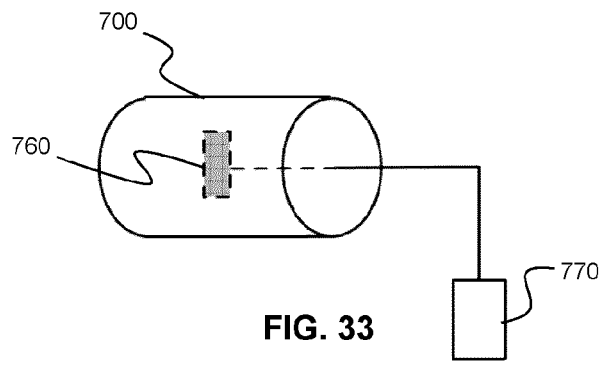
FIGS. 33-34 illustrate example implementations for electrically interfacing with an acoustic transducer housed within a noise isolating earplug.

With reference to FIG. 33, an example embodiment is illustrated with a vibration element 760 that is embedded inside the earplug. A non-limiting example of such an actuator is a piezoelectric crystal. This actuator could be oriented in such an orientation that the primary mode of vibrations are created in the perpendicular to the interface of the earplug and the ear canal. Alternatively, the actuator could be orientated such that vibrations are created to propagate in the direction of the axis of the earplug. A conducting wire, such as an insulated copper wire, is used to connect the vibration actuator to electronics 770 located outside the earplug that would create the signals to be actuated. An example of such electronics that would cause actuation of a piezoelectric crystal is a class G ceramic speaker driver such as the MAX9788 connected to a signal generator.

Figure 34:
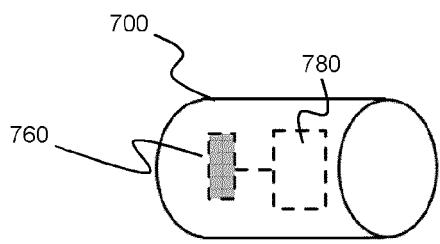

With reference to FIG. 34, an earplug 700 with an embedded actuator 760 and an embedded wireless module 780 is illustrated. Such a configuration would not require the use of any external wires. In this example, the wireless module could be a Bluetooth receiver module with an audio protocol. The electronics would also include a small battery, such as a lithium polymer battery to provide power to the electronics in the earbud.

Figure 35:
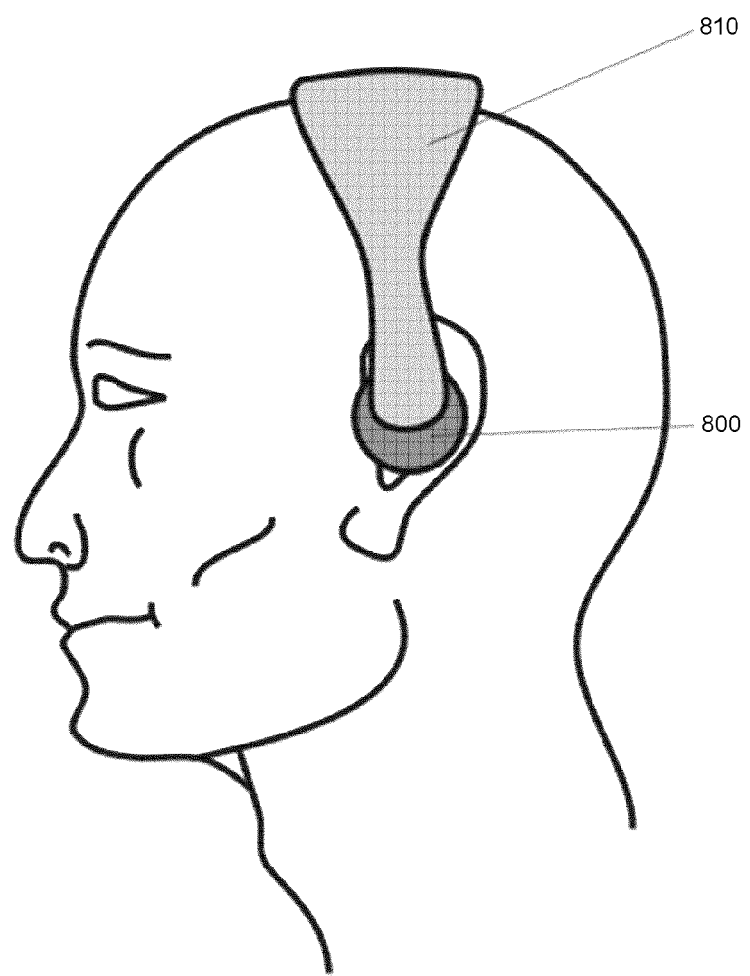
FIG. 35 illustrates an example embodiment in which vibration actuators are supported by a headphone band or earmuffs for contacting the vibration actuators with earplugs worn by a subject.

With reference to FIG. 35, an example embodiment of an over-the-head support is illustrated. Two vibration actuators 800 are attached to a flexible headband 810 that is worn by the wearer. The vibration actuators 810 make contact with earplugs worn by the wearer. The headband 810 applies pressure to the earplugs. One should note that while the vibration actuators are illustrated as being exposed, they could also be enclosed in a cavity or 'muff' that forms a seal over the ear to provide further passive noise protection for the wearer.

Figure 36A:
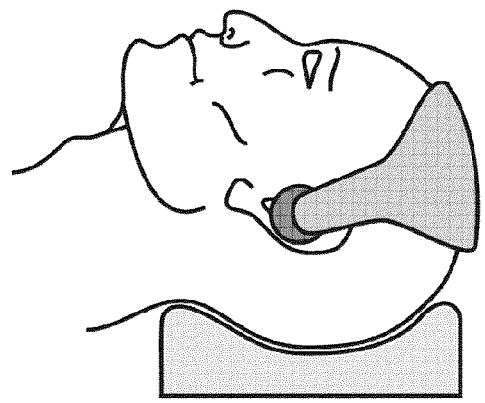
FIGS. 36A-B illustrate an example embodiment of a headset-based acoustic communication device that is sufficiently small to be used with a head coil of a magnetic resonance imaging scanner.
Figure 36B:
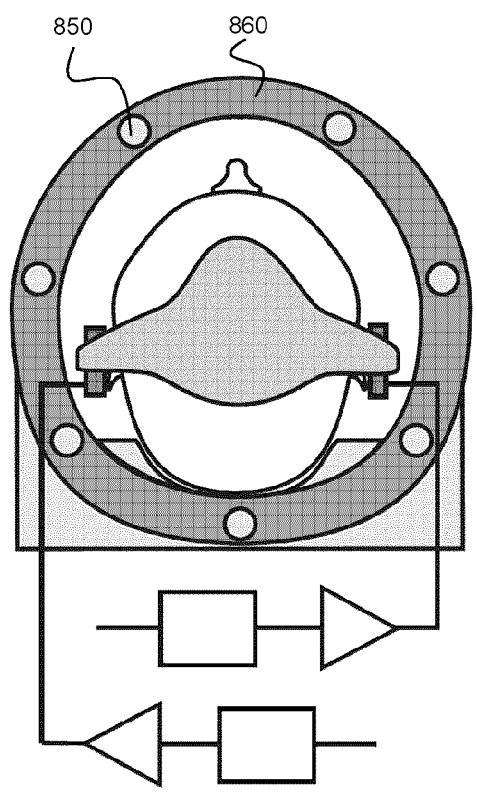

In order to allow the patient to benefit from the noise reduction yet permit scans of their head, the patient and communication devices may be configured fit inside a head coil. Such an example embodiment may be achieve with a head support similar to that of conventional headphones which drape over the top of the head as shown in FIGS. 35 and 36A. As viewed from the side (FIG. 36A), the headphone-type support is designed to prevent the vibration elements from sliding down away from the ears while the patient is laying horizontally and to provide adequate compression to the head to provide contact between the vibration elements and the ear plugs. As viewed from the top of the patient's head in FIG. 36B, this entire apparatus is sufficiently small to fit inside a head coil which is composed of head coil conductors 860 and the head coil housing 870.

It will be understood that although many of the aforementioned example embodiments have been described with reference to applications involving communication in an MRI environment, many of the embodiments disclosed above may be adapted for use in a wide range of other applications. For example, the active earplug embodiments described above that do not employ Lorentz acoustic transducer may be employed in applications beyond magnetic resonance imaging communication systems.

Furthermore, the headrest-based example embodiments described above may be employed in a wide range of medical applications beyond magnetic resonance imaging communications. For example, a headset could include fiducial markers for use in procedures involving image registration and/or surgical navigation, and/or be configured as a stereotactic frame with integrated speaker and/or microphone. In other example implementations, the headrest need not be used in a horizontal configuration, and may be used in an angled or upright configuration, such as a headrest in a vehicle or airplane. The headrest could also be adapted as a helmet, which could be used in applications with noisy environments such as, but not limited to, the military, factories, and operators of heavy machinery.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An acoustic communication device for use during magnetic resonance imaging, the acoustic communication device comprising:
   a headrest positionable within a magnetic resonance imaging scanner;
   a vibration actuator supported by said headrest, wherein said vibration actuator is supported such that vibrations produced therefrom are acoustically coupled to a passive earplug worn by a subject when the subject's head is supported by said headrest, and such that the vibrations acoustically coupled to the passive earplug are acoustically coupled to tissues surrounding an ear canal of the subject, thereby enabling the subject to hear the vibrations via bone conduction; and
   audio circuitry operably connected to said vibration actuator for sending audio signals thereto.

2. The acoustic communication device according to claim 1 wherein said vibration actuator is recessed within said headrest.

3. The acoustic communication device according to claim 2 wherein said vibration actuator is configured to contact the passive earplug when the subject's head is supported by said headrest.

4. The acoustic communication device according to claim 1 further comprising one or more acoustic impedance matching layers provided on said vibration actuator, such that when the subject's head is supported by said headrest, an outer surface of said one or more acoustic impedance matching layers contacts the passive earplug, and the vibrations generated by said vibration actuator are acoustically coupled to the passive earplug through the one or more acoustic impedance matching layers.

5. The acoustic communication device according to claim 1 wherein said vibration actuator is embedded within said headrest, such that the vibrations produced by said vibration actuator are conducted through an intermediate material prior to being acoustically coupled to the passive earplug via contact therewith.

6. The acoustic communication device according to claim 5 wherein said intermediate material is a portion of a cushioning material of said headrest.

7. The acoustic communication device according to claim 5 wherein said intermediate material is an acoustic conduit extending from said vibration actuator to a surface of said headrest, such that the vibrations acoustically conducted by said acoustic conduit are coupled to the passive earplug via contact therewith when the subject's head is supported by said headrest.

8. The acoustic communication device according to claim 7 wherein said vibration actuator resides within an acoustically isolating region defined within said headrest, wherein said acoustic conduit extends into said acoustically isolating region, such that the vibrations produced by said vibration actuator are acoustically coupled to the passive earplug through said acoustic conduit when the subject's head is supported by said headrest.

9. The acoustic communication device according to claim 1 wherein said vibration actuator supported by an outer surface of said headrest, such that the vibrations produced by said vibration actuator are conducted through an intermediate material within said headrest prior to being acoustically coupled to the passive earplug via contact therewith.

10. The acoustic communication device according to claim 1 further comprising a bone conduction microphone configured to detect speech of the subject when the subject's head is supported by said headrest.

11. The acoustic communication device according to claim 10 wherein said headrest comprises a base cushioning region configured to contact and support a rear portion of the subject's head, wherein said bone conduction microphone is supported by said base cushioning region.

12. The acoustic communication device according to claim 11 wherein said base cushioning region is formed from memory foam.

13. The acoustic communication device according to claim 11 wherein said headrest further comprises a support frame comprising:
   a pair of lateral support members configured to contact sides of the subject's head when the subject's head is supported by said headrest, wherein one of said lateral support members supports said vibration actuator; and
   a base support member supporting said base cushioning region.

14. The acoustic communication device according to claim 13 wherein said lateral support members are pivotally mounted to said base support member, and wherein said lateral support members are rotationally biased to maintain contact between said headrest and the passive earplug when the subject's head is supported by said headrest.

15. The acoustic communication device according to claim 14 wherein said lateral support members are translatable, in a direction parallel to a cranial-caudal direction, relative to said base cushioning region, in order to align said lateral support members with the subject's ears.

16. The acoustic communication device according to claim 11 wherein said headrest further comprises lateral cushioning regions located on either side of the subject's head when the subject's head is supported by said headrest, wherein said vibration actuator is supported by one of the lateral cushioning regions, and wherein an acoustically isolating channel is provided between said lateral cushioning region supporting said vibration actuator and said base cushioning region for reducing a sensitivity of said bone conduction microphone to the vibrations produced by said vibration actuator.

17. The acoustic communication device according to claim 11 wherein said base cushioning region is formed from a first material, and wherein a lateral region of said headrest that supports said vibration actuator is formed from a second material, and wherein said first material and said second material are selected to have different acoustic impedances for reducing a sensitivity of said bone conduction microphone to the vibrations produced by said vibration actuator.

18. The acoustic communication device according to claim 11 wherein said headrest further comprises an intermediate region located between said base cushioning region and a lateral region of said headrest that supports said vibration actuator, wherein an acoustic impedance of said intermediate region differs from the acoustic impedances of said base cushioning region and said lateral region, thereby reducing a sensitivity of said bone conduction microphone to the vibrations produced by said vibration actuator.

19. The acoustic communication device according to claim 1 wherein said headrest comprises lateral regions located on either side of the subject's head when the subject's head is supported by said headrest, and wherein said headrest further comprises a support frame configured to bias said lateral regions against the sides of the subject's head, such that contact is made between said headrest and the passive earplug.

20. The acoustic communication device according to claim 1 wherein said headrest further comprises a position adjustment mechanism for adjusting a location of said vibration actuator for accommodating different head sizes.

21. The acoustic communication device according to claim 1 wherein said headrest further comprises a magnetic resonance imaging head coil.

22. The acoustic communication device according to claim 1 wherein said headrest has a size that suitable for use within a magnetic resonance imaging head coil.

\* \* \* \* \*